United States Patent
Ostoja-Starzewski et al.

(10) Patent No.: US 6,433,112 B1
(45) Date of Patent: Aug. 13, 2002

(54) π-COMPLEX COMPOUNDS

(75) Inventors: Karl-Heinz Aleksander Ostoja-Starzewski, Bad Vilbel (DE); Warren Mark Kelly, Alberta (CA); Peter Schertl, Leverkusen (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/581,973

(22) PCT Filed: Dec. 10, 1998

(86) PCT No.: PCT/EP98/08074

§ 371 (c)(1), (2), (4) Date: Jul. 10, 2000

(87) PCT Pub. No.: WO99/33852

PCT Pub. Date: Jul. 8, 1999

(30) Foreign Application Priority Data

Dec. 23, 1997 (DE) .......................... 197 57 524

(51) Int. Cl.[7] .............................. C08F 4/44; B01J 31/38
(52) U.S. Cl. ........................ 526/160; 526/161; 526/171; 526/348.6; 526/943; 502/152; 502/155; 556/53
(58) Field of Search .................. 526/133, 160, 526/161, 172, 351, 348.6, 943; 502/104, 117, 152, 155; 556/53

(56) References Cited

U.S. PATENT DOCUMENTS

| 5,026,798 A | | 6/1991 | Canich .................. 526/127 |
|---|---|---|---|
| 5,444,145 A | * | 8/1995 | Brant et al. ............. 526/348.3 |
| 5,453,410 A | | 9/1995 | Kolthammer et al. ....... 502/155 |
| 5,453,475 A | | 9/1995 | Rieger et al. ............. 526/160 |
| 5,470,993 A | | 11/1995 | Devore et al. ............. 556/11 |
| 5,635,573 A | * | 6/1997 | Harrington et al. .......... 526/113 |
| 5,703,187 A | | 12/1997 | Timmers .................. 526/282 |
| 5,756,417 A | * | 5/1998 | De Boer et al. ............ 502/103 |
| 5,986,029 A | | 11/1999 | van Beek et al. ........... 526/160 |
| 6,013,819 A | | 1/2000 | Stevens et al. ............. 556/11 |

FOREIGN PATENT DOCUMENTS

| EP | 0 129 368 | | 7/1989 |
|---|---|---|---|
| EP | 0 638 593 A1 | * | 2/1995 |
| EP | 0 704 461 | | 2/1999 |
| WO | 94/20506 | | 9/1994 |

OTHER PUBLICATIONS

J. of Organometallic Chem. 29 (month unavailable) 1971, pp. 227–232, Abel et al, The Synthesis of Silyl–Disilyl–and Silylmethyl–Substituted π–Cyclopentadienyl Metal Carbonyls Via Organotin Intermediates.

J. of Organometallic Chem. 169 (month unavailable) 1979, pp. 327–353, Jutze et al, Sythese, Struktur und dynamisches Verhalten von Cyclopentadienylboranen.

J. Am. Chem. Soc. vol. 105, (month unavailable) 1983, p. 3382, (month unavailable).

Organometallic 1, (month unavailable) 1982, pp. 1591–1596, Casey et al, Heterobimetallic Compounds Linked by Heterodifunctional Ligands: Synthesis and X–ray Crystal Structure of $(CO)_4 MnMo(CO)_{3[\eta^5-C_5H_4P(C_6H_5)_2]}$.

J. Am. Chem. Soc. 104, (month unavailable) 1982, p. 2031.

* cited by examiner

*Primary Examiner*—David W. Wu
*Assistant Examiner*—R. Harlan
(74) *Attorney, Agent, or Firm*—Joseph C. Gil; Noland J. Cheung; Jennifer R. Seng

(57) ABSTRACT

The invention relates to novel π-complex compounds of transitional metals. The novel π-complex compounds are suitable for use as catalysts for the (co)polymerization of olefins, cyclo-olefins, alkynes, diolefins, vinyl ester and vinyl aromatics.

10 Claims, No Drawings

π-COMPLEX COMPOUNDS

FIELD OF THE INVENTION

The present invention relates to π complex compounds of transition metals which possess only one π ligand (half-sandwich structure) and which have a donor-acceptor bond, the donor group or the acceptor group being bonded to the transition metal. The coordinate bond existing between the donor atom and the acceptor atom produces a (partial) positive charge in the donor group and a (partial) negative charge in the acceptor group:

[donor group ⟶ acceptor group]

The invention further relates to a process for the preparation of such π complex compounds of transition metals and to their use as catalysts in processes for the homopolymerization or copolymerization of monomers.

BACKGROUND OF THE INVENTION

Metallocenes are known as π complex compounds of transition metals and their use as catalysts in the polymerization of olefins is also known (EP-A 129 368 and the literature cited therein). It is also known from EP-A'368 that metallocenes, in combination with alkylaluminium/water as cocatalysts, are effective systems for the polymerization of ethylene. Thus, for example, methylaluminoxane=MAO is formed from ca. 1 mole of trimethylaluminium and 1 mole of water; other stoichiometric proportions have also already been used successfully (WO 94/20 506). The cyclopentadienyl skeletons of such metallocenes were covalently linked together by a bridge. EP-A 704 461 may be mentioned as an example of the numerous patents and patent applications in this field; the linking group mentioned in said patent is a (substituted) methylene group or ethylene group, a silylene group, a substituted silylene group, a substituted germylene group or a substituted phosphine group. EP-A'461 also designates the bridged metallocenes as polymerization catalysts. π complex compounds suitable as polymerization catalysts are also already known which have only one π ligand. Examples which may be mentioned are: EP 416 815, U.S. Pat. Nos. 5,453,410, 5,470,993, WO 91/04257, WO 96/13529 and U.S. Pat. No. 5,453,475. In the half-sandwich structures described therein, bonds to a central transition metal are produced on the one hand by a cyclopentadienyl anion and on the other hand by a heteroatom, these two being covalently bonded together via a bridging group. As a result, such catalysts have a forced, strained geometric structure (CGC=Constrained Geometry Catalysts).

Catalysts of the last-mentioned type are outside the framework of the present invention.

Despite the numerous patents and patent applications in this field, there is still a desire for improved catalysts which are distinguished by special properties and high activity, so that the amount of catalyst remaining in the polymer can be kept small.

SUMMARY OF THE INVENTION

It has now been found that particularly advantageous catalysts can be prepared from π complex compounds of transition metals which have only one π ligand and which contain a donor-acceptor bond, there being a coordinate or so-called dative bond between the donor atom and the acceptor atom, which bond is at least formally superimposed by an ionic bond, the donor group or the acceptor group being bonded to the central metal. The π complex compounds according to the invention embrace at least two partial structures, depending on whether the donor atom D or the acceptor atom A is joined to the only π ligand.

DETAILED DESCRIPTION OF THE INVENTION

Accordingly, the invention relates to π complex compounds of transition metals of the formula

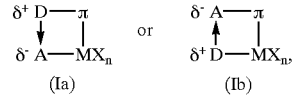

in which

π is a charged or electrically neutral π system which can be fused to one or two unsaturated or saturated five-membered or six-membered rings, and whose H atoms, in the fused or non-fused form, can be partially or completely replaced with identical or different radicals from the group comprising unbranched or branched $C_1$–$C_{20}$-(cyclo)alkyl, $C_1$–$C_{20}$-halogeno(cyclo)alkyl, $C_2$–$C_{20}$-(cyclo)alkenyl, $C_1$–$C_{20}$-(cyclo)alkoxy, $C_7$–$C_{15}$-aralkyl and $C_6$–$C_{12}$-aryl, or replaced in one or two instances with D or A, D is a donor atom which, in the case of partial structure (Ia), is a substituent or part of the π system or is bonded to the π system via a spacer and, in the case of partial structure (Ib), is bonded to the transition metal, A is an acceptor atom which, in the case of partial structure (Ia), is bonded to the transition metal and, in the case of partial structure (Ib), is a substituent or part of the π system or is bonded to the π system via a spacer, the bonding of D or A to the transition metal taking place either directly or via a spacer, D and A being linked via a coordinate bond in such a way that the donor atom takes on a (partial) positive charge and the acceptor atom a (partial) negative charge, and it being possible for D and A in turn to carry substituents, M is a transition metal of subgroup III to VIII of the periodic table of the elements (Mendeleeff), including the lanthanides and actinides, preferably of subgroup III to VI, including the lanthanides, and Ni, X is one anion equivalent and n is the number zero, one, two, three or four, depending on the charges of M and π, D and A being specifically defined as follows:
  i) in formula (Ia):
    D is disubstituted N, P, As, Sb or Bi or monosubstituted or disubstituted O, S, Se or Te, bonded to π via a spacer or directly, and
    A is B, Al, Ga or In, bonded to M via a spacer or directly; or
  ii) in formula (Ia), D and A together are one of the following groups bonded to π or M via a spacer or directly:

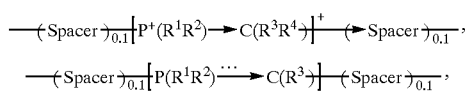

-continued

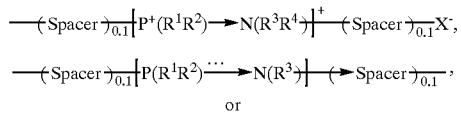

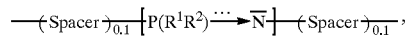

or

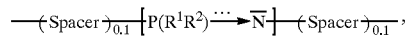

which represent phosphonium salts, phosphorus ylides, aminophosphonium salts and phosphinimines, or the corresponding ammonium salts and nitrogen ylides, arsonium salts and arsenic ylides sulfonium salts and sulfur ylides, selenium salts and selenium ylides, the corresponding aminoarsonium salts and arsinimines, aminosulfonium salts and sulfimines, aminoselenium salts and selenimines,

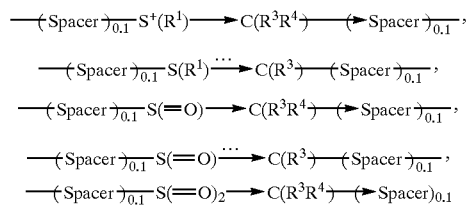

and the corresponding sulfimine structures; or iii) in formula (Ib):

D is disubstituted N, P, As, Sb or Bi or monosubstituted or disubstituted O, S, Se or Te, bonded to M via a spacer or directly, and A is disubstituted Al, Ga or In, bonded to π via a spacer or directly, or disubstituted B, bonded to π via a spacer, $R^1$, $R^2$, $R^3$ or $R^4$ and the expression "substituted" independently of one another are $C_1$–$C_{20}$-(cyclo)alkyl, $C_1$–$C_{20}$-halogeno(cyclo)alkyl, $C_2$–$C_{20}$-(cyclo)alkenyl, $C_7$–$C_{15}$-aralkyl, $C_6$–$C_{12}$-aryl, $C_1$–$C_{20}$-(cyclo)alkoxy, $C_7$–$C_{15}$-aralkoxy, $C_6$–$C_{12}$-arloxy, indenyl, halogen, 1-thienyl, disubstituted amino, trisubstituted silyl which can be bonded via —$CH_2$—, or phenylacetylenyl, and "Spacer" is a divalent sityl, germanyl, amino, phosphino, methylene, ethylene, propylene, disilylethylene or disiloxane group which can be monosubstituted to tetrasubstituted by $C_1$–$C_4$-alkyl, phenyl or $C_4$–$C_6$-cycloalkyl, and the element P, N, As, S or Se is bonded to π via the spacer or directly, a spacer being arranged between A and M in the case where D is part of the π system, and —$C(R^1)$= also occurring as a spacer in cases i) and ii).

The following, which are listed only by way of example and are not exhaustive, are important structures covered by formulae (Ia) and (Ib):

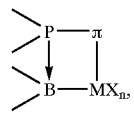 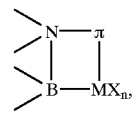 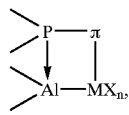

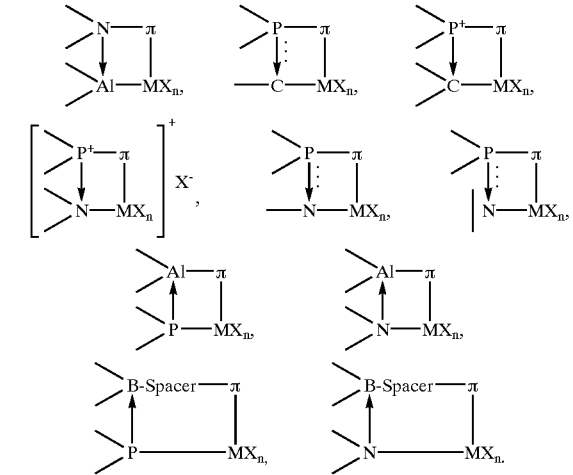

Preferred structures are those without spacers, with the exception of structures in which D is part of the π system, which always contain a spacer between A and M. Structures of partial formula (Ia) are also preferred.

The π complex compounds of transition metals according to the invention, of the above-described type (Ia or Ib) in the context of i) or iii), can be prepared, for example in a manner known to those skilled in the art, in such a way that, in the case of the partial structure of formula (Ia). either a compound of formula (II) is reacted with a compound of formula (III):

 (II)

and

 (III)

with the elimination of the compound YX (IV),
or a compound of formula (V) is reacted with a compound of formula (VI):

 (V)

and $MX_{n+1}$ (VI)

with the elimination of the compound YX (IV),
or a compound of formula (VII) is reacted with a compound of formula (VIII):

 (VII)

and

AY (VIII)

with the elimination of the compound YX (IV), and in the case of the partial structure of formula (Ib), either a compound of formula (IX) is reacted with a compound of formula (X):

  (IX)

and

D—MX$_{n+1}$  (X)

with the elimination of the compound YX (IV), or a compound of formula (XI) is reacted with a compound of formula (VI):

  (XI)

and

MX$_{n+1}$  (VI)

with the elimination of the compound YX (IV), or a compound of formula (XII) is reacted with a compound of formula (XIII):

  (XII)

and

DY  (XIII)

with the elimination of the compound YX (IV), in the presence or absence of an aprotic solvent, π, D, A, M, X and n being as defined above and Y being Si(R$^1$R$^2$R$^3$), Ge(R$^1$R$^2$R$^3$) or Sn(R$^1$R$^2$R$^3$), in which R$^1$, R$^2$ and R$^3$ independently of one another are linear or branched C$_1$–C$_{20}$-(cyclo)alkyl, C$_1$–C$_{20}$-halogeno(cyclo)alkyl, C$_2$–C$_{20}$-(cyclo)alkenyl, C$_7$–C$_{15}$-aralkyl, C$_6$–C$_{12}$-aryl, vinyl, allyl or halogen, it also being possible for Y to be one cation equivalent of an alkali (alkaline earth) metal or thallium in the case where π carries a negative charge, and it also being possible for Y to be hydrogen if X is an amide anion of the type R$_2$N$^-$, a carbanion of the type R$_3$C$^-$ or an alcoholate anion of the type RO$^-$.

The preparation of π complex compounds in the context of ii) of formula Ia, with the onium salts, ylides, aminoonium salts and imines contained therein, is also carried out in a manner know to those skilled in the art (A. W. Johnson, W. C. Kaska, K. A. Ostoja Starzewski, D. A. Dixon, Ylides and Imines of Phosphorus, John Wiley and Sons, Inc., New York 1993): phosphonium salts can be obtained by the quaternization of phosphines with organic halides. Dehydrohalogenation with bases in a stoichiometry of ca. 1:1 leads to phosphorus ylides. Reaction with further equivalents of base (e.g. butyllithium) gives the ylide anion with the elimination of butane:

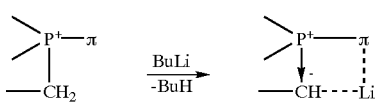

Further reaction with MX$_n$, with the elimination of LiX, leads to the D/A half-sandwich complex according to the invention:

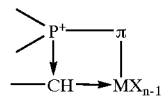

Another equivalent of base, with dehydrohalogenation, finally yields

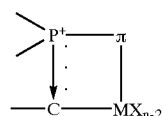

The isoelectronic (P→N) derivatives can be prepared analogously by starting from the aminophosphonium salts, or the starting material is a donor-substituted half-sandwich complex, e.g.

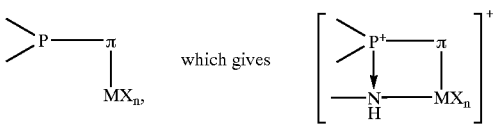

with organic amine and carbon tetrachloride. Subsequent deprotonation gives, in the first step,

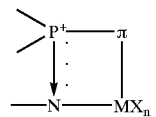

(which is also formed from the P-substituted half-sandwich complex by reaction with organic azides or triorganosilyl azides with the subsequent elimination of N$_2$) and, with further base,

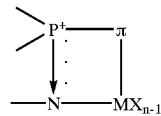

in the case where the nitrogen carries an H atom.

The invention further relates to the use of π complex compounds of transition metals of the above-described type (Ia or Ib) as catalysts in processes for the homopolymerization or copolymerization of monomers from the group comprising C$_2$–C$_{12}$-α-olefins, C$_4$–C$_{30}$-cycloolefins, C$_2$–C$_3$-alkynes, C$_4$–C$_3$-diolefins, C$_4$–C$_3$-vinyl esters and C$_8$–C$_{12}$-vinylaromatics, in the gas, solution, high-temperature solution, bulk, high-pressure or slurry phase, at −60° C. to +250° C. and 0.5 to 5000 bar, and in the presence or absence of saturated or aromatic hydrocarbons or saturated or aromatic halogenohydrocarbons, and in the presence or absence of hydrogen, the π complex compounds being used in an amount of $10^{-12}$ to $10^{-1}$ mole per mole of monomers, and it also being possible for the polymerization to be carried out in the presence of Lewis acids, Bronsted acids or Pearson acids or additionally in the presence of Lewis bases.

The donor atom D is an element of main group V or VI of the periodic table of the elements (Mendeleeff) and possesses at least one free electron pair in its particular bonding state. Examples of donor atoms are N, P, As, Sb, Bi, O, S, Se and Te, preferably N, P, As, O, S and Se and particularly preferably N, P and O. Donor atoms are in a bonding state with substituents in the case of elements of main group V and can be in such a state in the case of elements of main group VI. This is illustrated below using phosphorus and oxygen as examples of donor atoms, "Subst." representing said substituents and "π" representing the bond to the π system if the donor atom is bonded to the π system. The arrow denotes the coordinate bond through a first free electron pair, and other lines denote other available electron pairs:

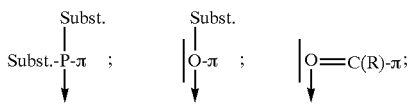

Acceptor atoms A are on the one hand elements of main group III of the periodic table of the elements (Mendeleeff), such as B, Al, Ga and In, preferably B, Al or Ga, which are in a bonding state with substituents and have an electron pair gap. On the other hand, the acceptor atom A includes elements of other main groups of the periodic table of the elements which, in their bonding state, form a group, selected from nitrene, carbene and carbyne groups, acting as an acceptor.

In its bonding state, the donor atom D forms the donor group, optionally with substituents; in its bonding state, the acceptor atom A forms the acceptor group with substituents. Thus the donor group is the unit comprising the donor atom D, the substituents, if present, and the available electron pairs; by analogy, the acceptor group is the unit comprising the acceptor atom A, the substituents and the available electron pair gaps. D and A are linked by a coordinate bond, D taking on a (partial) positive charge and A a (partial) negative charge.

Examples of substituents on the donor atoms N, P, As, Sb, Bi, O, S, Se or Te and on the acceptor atoms B, Al, Ga or In are: $C_1$–$C_{20}$-(cyclo)alkyl, $C_1$–$C_{20}$-halogeno(cyclo)alkyl, $C_1$–$C_{20}$-(cyclo)alkenyl, $C_7$–$C_{15}$-aralkyl, $C_6$–$C_{12}$-aryl, $C_1$–$C_{20}$-alkoxy, $C_6$–$C_{12}$-aryloxy, $C_7$–$C_{15}$-aralkoxy, indenyl, halogen, 1-thienyl, disubstituted amino, phenylacetylenyl, trisubstituted silyl such as $Si(CH_3)_3$, or trisubstituted silyl which is bonded to D or A via —$CH_2$—.

$C_1$–$C_{20}$-(Cyclo)alkyl is unbranched or branched and is, for example, methyl, ethyl, propyl, i-propyl, cyclopropyl, butyl, i-butyl, tert-butyl, cyclobutyl, pentyl, neopentyl, cyclopentyl, the isomeric hexyls, cyclohexyl, the isomeric heptyls, cycloheptyl, the isomeric octyls, cyclooctyl, the isomeric nonyls, decyl, undecyl, dodecyl, hexadecyl, octadecyl or eicosyl. Preferred alkyl has 1 to 6 C atoms; preferred cycloalkyl has 5 or 6 C atoms.

$C_1$–$C_{20}$-Halogeno(cyclo)alkyl is derived from said unsubstituted (cyclo)alkyls in that the H atoms are partially or completely substituted by halogen, preferably fluorine or chlorine.

$C_1$–$C_{20}$-Alkoxy substituents are derived from said $C_1$–$C_{20}$-(cyclo)alkyls in that they are bonded via an ether oxygen.

$C_2$–$C_{20}$-(Cyclo)alkenyl is linear or branched and is, for example, vinyl, allyl, butenyl, pentenyl, cyclopentenyl, hexenyl, cyclohexenyl or other $C_2$–$C_{20}$-(cyclo)alkenyls which differ from said (cyclo)alkyls by a terminal or internal double bond.

$C_7$–$C_{15}$-Aralkyl is, for example, tolyl, α- and β-phenylethyl, phenylpropyl, phenylbutyl, 1- and 2-naphthylmethyl, 1- and 2-naphthylethyl, anthrylmethyl, biphenylylmethyl or other $C_7$–$C_{15}$-aralkyls known to those skilled in the art.

$C_6$–$C_{12}$-Aryl is, for example, phenyl, 1- and 2-naphthyl or biphenylyl.

Aryloxy and aralkoxy are derived from said aryl and aralkyl radicals in that they are bonded via an ether oxygen.

The aromatic radicals contained in said substituents can be monosubstituted, disubstituted or polysubstituted by $C_1$–$C_4$-alkyl groups, $C_1$–$C_4$-alkoxy groups, $C_1$–$C_4$-halogenoalkyl groups, halogen, nitro, $C_1$–$C_6$-alkylcarboxyl, $C_1$–$C_6$-alkylcarbonyloxy, $C_1$–$C_6$-alkylcarbonyl, cyano, the sulfonic acid group or the neutralized sulfonic acid group, or several of these.

Halogen is, for example, fluorine, chlorine, bromine or iodine, preferably fluorine or chlorine.

Disubstituted amino can carry $C_1$–$C_{12}$-alkyl substituents, $C_6$–$C_{12}$-aryl substituents, $C_7$–$C_{15}$-aralkyl substituents or two different substituents of said type.

Trisubstituted silyl can carry $C_1$–$C_{20}$-alkyl substituents, $C_6$–$C_{12}$-aryl substituents, $C_7$–$C_{15}$-aralkyl substituents or a mixture of different substituents from those mentioned. Such silyl groups can also be bonded via a methylene group, an example being $(CH_3)_3SiCH_2$—.

Preferred substituents of those mentioned are $C_1$–$C_6$-alkyl, $C_5$–$C_6$-cycloalkyl, phenyl, tolyl, $C_1$–$C_6$-alkoxy, $C_6$–$C_{12}$-aryloxy, vinyl, allyl, benzyl, perfluorophenyl, fluorine, chlorine, di($C_1$–$C_6$-alkyl)amino and diphenylamino.

Examples of preferred donor groups are $(CH_3)_2N$—, $(C_2H_5)_2N$—, $(C_3H_7)_2N$—, $(C_4H_9)_2N$—, $(C_6H_5)_2N$—, $(CH_3)_2P$—, $(C_2H_5)_2P$—, $(C_3H_7)_2P$—, (i-$C_3H_7)_2P$—, $(C_4H_9)_2P$—, (t-$C_4H_9)_2P$—, (cyclohexyl)$_2P$—, $(C_6H_5)_2P$—, $(CH_3)(C_6H_5)P$—, $Cl_2P$—, $CH_3O$—, $CH_3S$—, $C_6H_5S$—, $C_6H_5CO$—, $CH_3CO$—, $(CH_3)_3Si$—O— and t-butyl-$(CH_3)_2Si$—O—, in which N and P each carry one free electron pair and O and S each carry two free electron pairs, the double-bonded oxygen in some examples being bonded via a spacer group, and systems, like the pyrrolidone ring, in which the ring members other than N also act as spacers.

Examples of preferred acceptor groups are $(CH_3)_2B$—, $(C_2H_5)_2B$—, $H_2B$—, $(C_6H_5)_2B$—, $CH_3(C_6H_5)B$—, (vinyl)$_2B$—, (benzyl)$_2B$—, $Cl_2B$—, $(CH_3O)_2B$—, $Cl_2Al$—, $(CH_3)_2Al$—, (i-$C_4H_9)_2Al$—, $(Cl)(C_2H_5)Al$—, $(CH_3)_2Ga$—, $(C_3H_7)_2Ga$—, $((CH_3)_3Si$—$CH_2)_2Ga$—, (vinyl)$_2Ga$—, $(C_6H_5)_2Ga$—, $(CH_3)_2In$—, $((CH_3)_3Si$—$CH_2)_2In$— and (cyclopentadienyl)$_2In$—. Of said species, those in which 1 or more H atoms are replaced with fluorine are also suitable.

Other suitable donor and acceptor groups are those which contain chiral centres and in which two substituents form a ring with the D or A atom, possible examples being

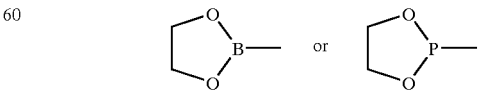

The following are examples of preferred donor-acceptor bonds: N→B, N→Al, P→B, P→Al, O→B, O→Al, C=O→B, C=O→Al, P→C and P→N.

One of D and A is bonded to the π system, while the other is bonded to the metal M. Thus the donor atom D is bonded to the π system in the case of partial structure (Ia), while the acceptor atom A is bonded to the π system in the case of partial structure (Ib).

In the case where it is bonded to the π system, D or A can be a substituent of the π system or part of the π system, or it can be bonded to the π system via a spacer; the latter case also amounts to a substituent of the π system, said substituent merely being extended by the spacer group.

The case where D or A is linked to the π system via a spacer can be represented as follows: D-Spacer-π or A-Spacer-π. Thus, for example, in the above examples of formulae, the moiety =C(R)— represents such a spacer between O and π. Examples of such spacer groups are: dimethylsilyl, diethylsilyl, di-n-propylsilyl, di-1-propylsilyl, di-n-butylsilyl, di-t-butylsilyl, di-n-hexylsilyl, methylphenylsilyl, ethylmethylsilyl, diphenylsilyl, di(p-t-butylphenethyl)silyl, n-hexylmethylsilyl, cyclopentamethylenesilyl, cyclotetramethylenesilyl, cyclotrimethylenesilyl, dimethylgermanyl, diethylgermanyl, phenylamino, t-butylamino, methylamino, t-butylphosphino, ethylphosphino, phenylphosphino, methylene, dimethylmethylene (i-propylidene), diethylmethylene, ethylene, dimethylethylene, diethylethylene, dipropylethylene, propylene, dimethylpropylene, diethylpropylene, 1,1-dimethyl-3,3-dimethylpropylene, tetramethyldisiloxane, 1,1,4,4-tetramethyldisilylethylene and diphenylmethylene. Preferably, D and A are bonded without spacers to the π system.

In the case where D or A is a substituent of the π system, they can be located directly on the π system, on a fused 5-membered or 6-membered ring or on another substituent of the π system. Where there are several D or A groups, these can occupy different positions among those mentioned.

In the case where D or A is part of the π system, heteroatomic π systems are obtained. Accordingly, the π systems can be carbocyclic (if D or A is a substituent of the π system) or heterocyclic (if D or A is part of the π system), open-chain carbon π systems or heteroatomic π systems. These π systems can be electrically charged or neutral. They can also be fused with one or two unsaturated or saturated 5-membered or 6-membered rings. Examples of such fused rings are the benzene ring, the 1- or 2-naphthyl system or a cyclopentyl or cyclohexyl ring. The π system is further characterized in that the H atoms in the entire system can be partially or completely replaced with identical or different radicals from the group comprising unbranched or branched $C_1$–$C_{20}$-(cyclo)alkyl, $C_1$–$C_{20}$-halogeno(cyclo)alkyl, $C_2$–$C_{20}$-(cyclo)alkenyl, $C_7$–$C_{15}$-aralkyl and $C_6$–$C_{12}$-aryl, or one or two H atoms can be replaced with D or A of the type described above.

π systems according to the invention are substituted and unsubstituted ethylene, allyl, pentadienyl, benzyl, butadiene, benzene, the cyclopentadienyl anion, the cyclooctatetraene bisanion and the species obtained by replacing at least one C atom with a heteroatom. Of said species, those which are cyclic are preferred. The nature of the coordination of such π systems (ligands) to the metal can be of the σ type or of the π type.

Examples of carboxylic π systems are cyclopentadiene, substituted cyclopentadiene, indene, substituted indene, fluorene and substituted fluorene, which can be further substituted in the manner indicated. In the form of their anions, such skeletons containing cyclopentadiene are excellent ligands for transition metal complexes, the cyclopentadienyl carbanion compensating one positive charge of the transition metal. Specific examples of such carbanions are: cyclopentadienyl, methylcyclopentadienyl, 1,2-dimethylcyclopentadienyl, 1,3-dimethylcyclopentadienyl, 1,2-diethylcyclopentadienyl, tetramethylcyclopentadienyl, ethylcyclopentadienyl, n-butylcyclopentadienyl, n-octylcyclopentadienyl, β-phenylpropylcyclopentadienyl, propylcyclopentadienyl, t-butylcyclopentadienyl, benzylcyclopentadienyl, diphenylmethylcyclopentadienyl, trimethylgermylcyclopentadienyl, trimethylstannylcyclopentadienyl, trifluoromethylcyclopentadienyl, trimethylsilylcyclopentadienyl, pentamethylcyclopentadienyl, N,N-dimethylaminocyclopentadienyl, dimethylphosphinocyclopentadienyl, methoxycyclopentadienyl, dimethylboranylcyclopentadienyl, (N,N-dimethylaminomethyl)cyclopentadienyl, indenyl, phenylindenyl, tetrahydroindenyl, fluorenyl, tetrahydro- or octahydro-fluorenyl, and fluorenyls and indenyls benzofused on the 6-membered ring.

Examples of heterocyclic π systems in which D or A is part of the ring system are:

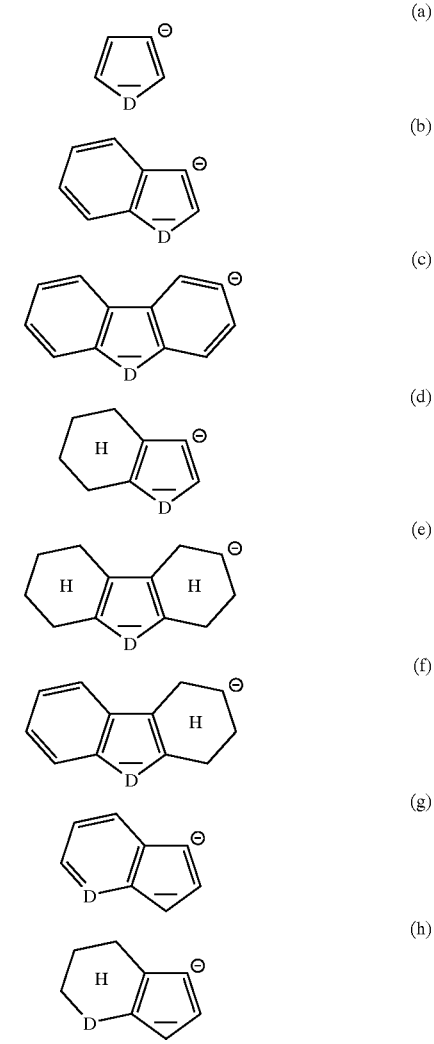

-continued

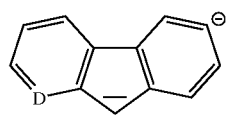 (i)

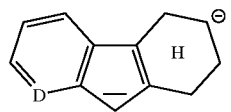 (j)

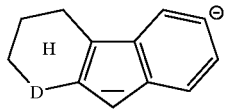 (k)

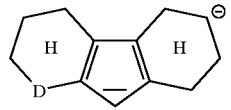 (l)

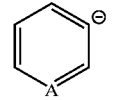 (m)

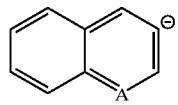 (n)

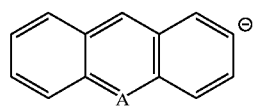 (o)

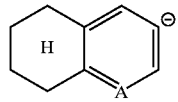 (p)

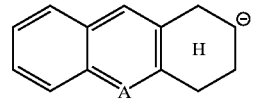 (q)

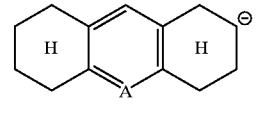 (r)

Important heterocyclic ring systems are the systems denoted by (a), (b), (c), (d), (g), (m), (n) and (o); those denoted by (a), (b), (c) and (m) are particularly important.

In the case where one of D and A is a substituent of its corresponding ring system, the latter is 3-, 4-, 5-, 6-, 7- or 8-membered, with or without electrical charge, and can be further substituted and/or fused in the manner indicated. 5-membered and 6-membered ring systems are preferred. The negatively charged cyclopentadienyl system is particularly preferred.

Examples of heterocycles on which such π complexes are based and which contain a donor atom from main group 5 or 6 of the periodic table of the elements (Mendeleeff) are: pyrrole, methylpyrrole, dimethylpyrrole, trimethylpyrrole, tetramethylpyrrole, t-butylpyrrole, di-t-butylpyrrole, indole, methylindole, dimethylindole, t-butylindole, di-t-butylindole, tetramethylphosphole, tetraphenylphosphole, triphenylphosphole, trimethylphosphole, phosphaindene, dibenzophosphole (phosphafluorene), dibenzopyrrole, furan, thiophene, coumarone, thionaphthene, carbazole, diphenylene oxide, diphenylene sulfide and pyridine.

An example of a heterocyclic π system which contains an acceptor atom A as part of the system is borabenzene.

Examples of open-chain heteroatomic π complexes are:

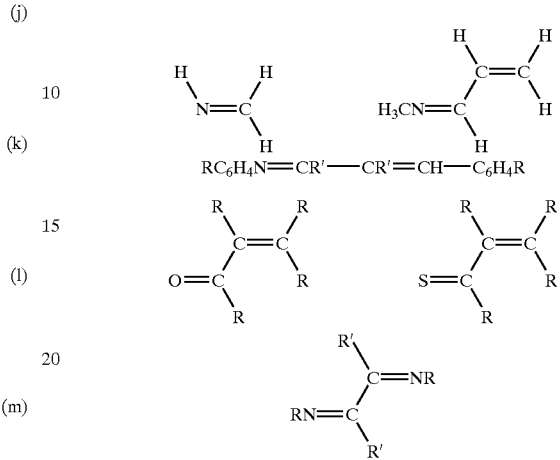

R, R'=H, alkyl, aryl, alkaryl, e.g. methyl, ethyl, t-butyl, phenyl or o,o'-di-(i-propyl)phenyl Apart from the substituents mentioned above, the π system can additionally be monosubstituted or disubstituted by D or A.

M is a transition metal of subgroup III to VIII of the periodic table of the elements (Mendeleeff), including the lanthanides and actinides, and preferably of subgroup III to VI, including the lanthanides, and Ni; examples which may be mentioned are: Sc, Y, La, Sm, Nd, Lu, Ti, Zr, Hf, Th, V, Nb, Ta and Cr. Of these, Ti, Zr, Hf, V, Nb, Cr and Ta are preferred and Ti, Zr and Hf are particularly preferred. Said transition metals can occur in the π complexes according to the invention in various of their known valence states.

In the formation of the π complex structure, one positive charge of the transition metal M is compensated by the π complex in the case where the π complex carries an anionic charge. In the case of electrically neutral π systems, no positive charge of the transition metal M is compensated. In all cases, positive charges still remaining on the transition metal M are neutralized by mostly monovalent anions X. Examples of X are: hydride, chloride, methyl, ethyl, phenyl, fluoride, bromide, iodide, the n-propyl radical, the i-propyl radical, the n-butyl radical, the amyl radical, the i-amyl radical, the hexyl radical, the i-butyl radical, the heptyl radical, the octyl radical, the nonyl radical, the decyl radical, the cetyl radical, methoxy, ethoxy, propoxy, butoxy, phenoxy, dimethylamino, diethylamino, di-t-butylamino, diphenylamino, diphenylphosphino, dicyclohexylphosphino, dimethylphosphino, methylidene, ethylidene and propylidene. Two identical or different monovalent anions can also be linked together (dianions-⌒-)

for example singly or doubly charged negative radicals made up of identical or different, linear or branched, saturated or unsaturated hydrocarbons, amines, phosphines, thioalcohols, alcohols or phenols. Two monoanions, such as $CR_3^{\ominus}$, $NR_2^{\ominus}$, $PR_2^{\ominus}$, $OR^{\ominus}$, $SR^{\ominus}$ etc., can be joined together by saturated or unsaturated hydrocarbon or silane bridges to form such dianions, and the number of bridging atoms can be 0, 1, 2, 3, 4, 5 or 6, 0 to 4 bridging atoms being preferred and 1 or 2 bridging atoms being particularly preferred. Apart from H atoms, these bridging atoms can also carry further hydrocarbon substituents. Possible examples of bridges between the monoanions are —CH$_2$—, —CH$_2$—CH$_2$—, —(CH$_2$)$_3$—, —CH=CH—, —(CH=CH)$_2$—, —CH=CH—CH$_2$—, CH$_2$—CH=CH—CH$_2$—, —Si(CH$_3$)$_2$— and —C(CH$_3$)$_2$—. Examples of dianions are 1,4-diphenyl-1,3-butadienediyl, 3-methyl-1,3-pentadienediyl, 1,4-dibenzyl-1,3-butadienediyl, 2,4-hexadienediyl, 1,3-pentadienediyl, 1,4-ditolyl-1,3-butadienediyl, 1,4-bis(trimethylsilyl)-1,3-butadienediyl, 1,3-butadienediyl and the ethylene glycol dianion. 1,4-Diphenyl-1,3-butadienediyl, 1,3-pentadienediyl, 1,4-dibenzyl-1,3-butadienediyl, 2,4-hexadienediyl, 3-methyl-1,3-pentadienediyl, 1,4-ditolyl-1,3-butadienediyl and 1,4-bis(trimethylsilyl)-1,3-butadienediyl are particularly preferred. Other examples of dianions are those with heteroatoms, for instance of the structure

the bridge denoted by the curved line being as defined. Additionally, weakly coordinating or non-coordinating anions of the type mentioned below are particularly preferred for charge compensation.

Depending on the charge of M, that of the π complex and the nature of the direct bond between A and M in the case of partial structure (Ia) or of the bond between D and M in the case of partial structure (Ib), the subscript n takes the value zero, one, two, three or four, preferably zero, one or two. Thus, depending inter alia on which of the various subgroups they belong to, the above-mentioned transition metals can have valences/charges of two to six, preferably two to four, two of which can be compensated in the case of charged π complexes and a direct bond A—M or D—M. Accordingly, the subscript n takes the value one in the case of La$^{3+}$, for example, and the value two in the case of Zr$^{4+}$, for example; n zero for Sm$^{2+}$, for example.

The π complex compounds of transition metals of formula (Ia) or (Ib) can be prepared in the case of the partial structure of formula (Ia) by reacting either a compound of formula (II) with a compound of formula (III), or a compound of formula (V) above with a compound of formula (VI) above, or a compound of formula (VII) above with a compound of formula (VIII) above, always with the elimination of the compound YX (IV), and in the case of the partial structure of formula (Ib) by reacting either a compound of formula (IX) with a compound of formula (X), or a compound of formula (XI) with a compound of formula (VI), or a compound of formula (XII) with a compound of formula (XIII), always with the elimination of the compound YX (IV). This reaction is carried out in the presence or absence of an aprotic solvent, in the temperature range from −78° C. to +120° C., preferably in the range from −40° C. to +70° C., and in a molar ratio (II):(III), (V):(VI), (VII):(VIII, (IX):(X), (XI):(VI) or (XII):(XIII) of 1:0.5 to 2, preferably 1:0.8 to 1.25 and particularly preferably 1:1. In cases where both reactants are liquid, or where at least one is liquid under the reaction conditions and is capable of dissolving or suspending the other, and/or the reaction product is also liquid, it is possible to dispense with the concomitant use of a solvent. Provided it is a liquid, the eliminated compound YX (IV) can also serve to maintain the liquid phase in the reaction according to the invention without the use of a solvent.

Y is the radical of a silane, a germane or a stannane as defined above. In the case where the π complex carries a negative charge, Y can also be one cation equivalent of an alkali (alkaline earth) metal or thallium. Finally, Y can also be hydrogen if X is an amide anion of the type R$_2$N$^-$, a carbanion of the type R$_3$C$^-$ or an alcoholate anion of the type RO$^-$.

Thus the eliminated compound YX can be, for example, trimethylchlorosilane, triethylchlorosilane, tri(n-butyl)chlorosilane, triphenylchlorosilane, trimethylchlorogermane, trimethylchlorostannane, TlCl, LiCl, LiBr, LiF, LiI, NaCl, NaBr, KCl, KF, MgCl$_2$, MgBr$_2$, CaCl$_2$, CaF$_2$, an amine R$_2$NH or R$_2$NY, a hydrocarbon compound of the formula R$_3$CH or R$_3$CY, or an ether ROY, in which Y is Si(R$^1$R$^2$R$^3$), Ge(R$^1$R$^2$R$^3$) or Sn(R$^1$R$^2$R$^3$). Accordingly, further examples of the compounds YX are dimethylamine, diethylamine, di(n-propyl)amine, di(i-propyl)amine, di(t-butyl)amine, t-butylamine, cyclohexylamine, aniline, methylphenylamine, diallylamine, methane, toluene, trimethylsilylamine, trimethylsilyl ether, tetramethylsilane and analogous compounds familiar to those skilled in the art.

In the reaction according to the invention, one component having a readily cleavable leaving group Y is reacted with one compound having a transition metal and at least one replaceable anion X. The readily cleavable leaving group can be located here on a π system with an associated donor atom (II) or with an associated acceptor atom A (IX) or on a c complex with an already preformed D/A bond (V) or (XI). However, the readily cleavable leaving group can also be introduced into the process in the form of a compound with the (substituted) donor atom D (XIII) or as a compound with the (substituted) acceptor atom A (VIII). The transition metal is introduced into the reaction in a symmetrical form thereto.

Both the starting materials of the preparative process, namely (II), (V), (VII), (IX), (XI) or (XII) on the one hand and (III), (VI), (VIII), (X) or (XIII), react spontaneously when brought together, with the simultaneous formation of the donor-acceptor bond, if this has not already been preformed, or with the simultaneous complexation of the transition metal, and with the elimination of the compound YX.

For the sake of clarity, the substituents on D and A have been omitted in the formula representation of the donor-acceptor bond.

In the case of the concomitant use of solvents in the preparative process according to the invention, these are polar or non-polar aprotic solvents such as aliphatic and aromatic hydrocarbons or aliphatic and aromatic halogenohydrocarbons. In principle, other aprotic solvents, such as those known to those skilled in the art, can also be used, although those with excessively high boiling points are less preferable in terms of the ease of working-up. Typical examples are: n-hexane, cyclohexane, pentane, heptane, petroleum ether, toluene, benzene, chlorobenzene, methylene chloride, diethyl ether, tetrahydrofuran and ethylene glycol dimethyl ether.

The starting materials for the process according to the invention can be prepared by processes known in the literature or by analogous processes. Thus, for example, analogously to J. of Organometallic Chem. 29, (1971), 227, the commercially available trimethylsilylcyclopentadiene can be reacted first with butyllithium and then with trimethylsilyl chloride to give bis(trimethylsilyl)cyclopentadiene. This in turn can be reacted with boron trichloride to give trimethylsilylcyclopentadienyldichloroborane (analogously to J. of Organometallic Chem. 169, (1979), 327), which can finally be reacted with titanium tetrachloride to give dichloroborylcyclopentadienyltitanium trichloride analogously to J. of Organometallic Chem. 169, (1979), 373. This last-mentioned compound is covered by formula (XII) above. By reaction with trimethylaluminium, the two chlorine atoms bonded to the boron atom can be exchanged for methyl groups. Analogously to the descriptions of processes in J. Am. Chem. Soc. 105, (1983), 3882 and Organometallics 1, (1982), 1591, the commercially available cyclopentadienylthallium can be reacted with chlorodiphenylphosphine and further with butyllithium to give precursors of formula (VII). Another example which may be mentioned is the formation of dimethylstannyldiphenylphosphinoindene by reacting indene first with butyllithium, as already mentioned above, and then with chlorodiphenylphosphine; further reaction, first with butyllithium again and then with chlorotributyltin, gives the target compound, which, after further reaction with zirconium tetrachloride, gives diphenylphosphinoindenylzirconium trichloride as a representative of formula (VII). Such syntheses and preparative procedures are familiar to those skilled in the art who work in the field of metal-organic and element-organic chemistry, and are published in numerous literature references, only a few of which have been cited above as examples. The examples listed at the end of the general description show how heterocyclic precursors are obtainable for the π complex compounds of transition metals according to the invention. Thus pyrrolyllithium can be prepared from pyrrole by reaction with butyllithium, for instance as described in J. Am. Chem. Soc. 104, (1982), 2031. Trimethylstannylphosphole is obtained by reacting 1-phenylphosphole with lithium and then with aluminium trichloride to give phospholyllithium, which in turn reacts further with trimethylchlorostannane to give trimethylstannylphosphole (cf. J. Chem. Soc., Chem. Comm. 1988, 770). This compound can be reacted with titanium tetrachloride to give phospholyltitanium trichloride. Analogously, known preparative processes exist for open-chain π complex compounds made up of carbon atoms only or with incorporated heteroatoms, which can be provided with donor groups or acceptor groups analogously to the methods mentioned.

The onium salt, ylide/imine and ylide anion/imine anion structures mentioned above in connection with ii) in the context of formula (Ia) can be synthesized by processes known to those skilled in the art (cf. literature cited above).

The π complex compounds of transition metals of formulae (Ia) and (Ib) according to the invention can be used as catalysts in polymerization processes. Such homopolymerization or copolymerization processes are carried out in the gas, solution, high-temperature solution, bulk, high-pressure or slurry phase at −60 to +250° C., preferably 0 to 200° C., and 0.5 to 5000 bar, preferably 1 to 3000 bar, in the presence or absence of saturated or aromatic hydrocarbons or saturated or aromatic halogenohydrocarbons, and in the presence or absence of hydrogen, the π complex compounds being used in an amount of $10^{-2}$ to $10^{-1}$ mole per mole of monomers. Such polymerization processes can be carried out batchwise or, preferably, continuously. Likewise, the polymerization can be carried out in a semibatch process. Such processes can also be carried out in more than one reactor or more than one reaction zone. If several reaction zones are involved, it is possible to employ different polymerization conditions therein. Thus, in one reactor, it is possible to form a prepolymer which, in subsequent reactors, is particularly suitable as a heterogeneous catalyst for the actual (co)polymerization. Insoluble heterogeneous D/A catalysts in the form of the π complex compounds according to the invention on inorganic supports are particularly suitable for the formation of such prepolymers.

The π complex compounds according to the invention can be employed for the (co)polymerization in the isolated form as pure substances, but they can also be produced and used "in situ" in the (co)polymerization reactor in a manner known to those skilled in the art. The π complex compounds according to the invention can be present in both mononuclear and polynuclear form.

According to the invention, the π complex compounds can also be used in the presence of Lewis acids, Brönsted acids or Pearson acids or additionally in the presence of Lewis bases. Examples of such Lewis acids are boranes or alanes such as alkylaluminium compounds, aluminium halides, aluminium alcoholates, organoboron compounds, boron halides, boric acid esters or boron or aluminium compounds containing both halide and alkyl, aryl or alcoholate substituents, as well as mixtures thereof, or the triphenylmethyl cation. Aluminoxanes or mixtures of aluminium-containing Lewis acids with water are particularly preferred. According to current knowledge, all acids work as ionizing agents to form a π complex cation which is charge-compensated by a bulky, poorly coordinating anion. Such compounds act as cocatalysts. Other cocatalysts apart from those mentioned are alkyllithium compounds, organomagnesium compounds such as Grignard compounds, or partially hydrolyzed organoboron compounds. Preferred cocatalysts are aluminoxanes. Examples of aluminoxane compounds are those of the formula

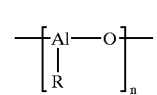

(XIV)

in which

R is $C_1$–$C_{20}$-alkyl, $C_6$–$C_{12}$-aryl or benzyl and n is a number from 2 to 50, preferably 10 to 35.

It is also possible to use a mixture of different aluminoxanes or a mixture of their precursors (alkylaluminium compounds) in combination with water (in gaseous, liquid, solid or bound form, for instance as water of crystallization). The water can also be introduced as (residual) moisture in the polymerization medium, the monomer or a support like silica gel. The boron compounds analogous to formula (XIV) are suitable as well. The bonds projecting from the square brackets of formula (XIV) carry R groups or $AIR_2$ groups as end groups of the oligomeric aluminoxane. Such aluminoxanes are normally present as a mixture of several with different chain lengths. Detailed study has also revealed aluminoxanes of cyclic or cage-like structure. Aluminoxanes are commercially available compounds. In the special case where $R=CH_3$, they are referred to as methylaluminoxanes (MAO).

The activation with the cocatalyst or the production of the bulky non-coordinating or weakly coordinating anion can be carried out in an autoclave or in a separate reaction vessel (preformation). The activation can be effected in the presence or absence of the monomer(s) to be polymerized. The activation can be carried out in an aliphatic, aromatic or halogenated solvent or suspending agent.

The π complex compounds or metallocene compounds and the aluminoxanes can be used either as such in homogeneous form or individually or together in heterogeneous form on supports. Said support can be of an inorganic or organic nature, such as silica gel, $Al_2O_3$, $MgCl_2$, NaCl, $B_2O_3$, polysiloxanes, cellulose derivatives, cyclodextrins, starch derivatives and other polymers like polyethylene or polypropylene. It is possible here to apply either the π complex compound or metallocene compound first or to apply the aluminoxane first to the support and then to add the other component. By the same token, however, it is also possible to activate the π complex compound or metallocene compound in homogeneous or heterogeneous form with the aluminoxane and then to apply the activated metallocene compound to the support, which is optionally loaded with aluminoxane.

The supports are preferably thermally and/or chemically pretreated in order to adjust the water content or the OH group concentration to a defined value or keep it as low as possible. A chemical pretreatment can consist e.g. in the reaction of the support with alkylaluminium compound. Inorganic supports are usually heated at 100° C. to 1000° C. for 1 to 100 hours before use. The surface area of such inorganic supports, especially of silica ($SiO_2$), is between 10 and 1000 $m^2/g$, preferably between 100 and 800 $m^2/g$. The particle diameter is between 0.1 and 500 micrometres ($\mu$), preferably between 10 and 200$\mu$.

The relative proportions of π complex compounds and cocatalyst are 1 to 100,000 mole of cocatalyst per mole of π complex compound.

According to the invention, it is also possible to use the reaction products of the above-described ionizing agents with π complex compounds of formulae (Ia) to (Id). They can be described by formulae (XVa) to (XVd):

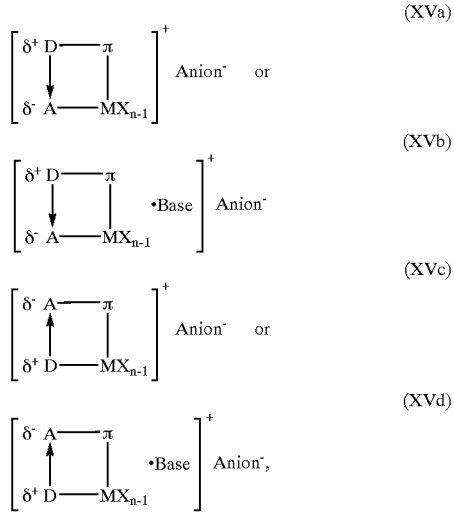

Base represents a Lewis base.

Examples of poorly coordinating anions are borates and alanates, for example:

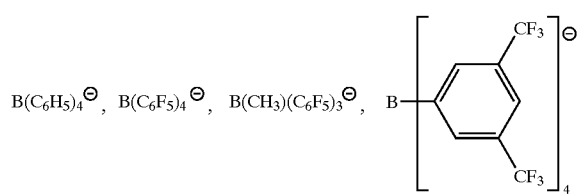

sulfonates such as tosylate or triflate, tetrafluoroborates, hexafluorophosphates, hexafluoroantimonates, perchlorates and bulky cluster molecular anions of the carborane type, for example $C_2B_9H_{12}^{\ominus}$ or $CB_{11}H_{12}^{\ominus}$. When such anions are present, metallocene compounds can also work as high-efficiency polymerization catalysts in the absence of aluminoxane. This is the case particularly when one π ligand is an alkyl group, allyl or benzyl. It can also be advantageous, however, to use such metallocene complexes with bulky anions in combination with alkylaluminium compounds such as $(CH_3)_3Al$, $(C_2H_5)_3Al$, (n-/i-propyl)$_3Al$, (n-/t-butyl)$_3Al$, (i-butyl)$_3Al$ or the isomeric pentyl-, hexyl- or octyl-aluminium compounds, alkyllithium compounds such as methyl-Li, benzyl-Li or butyl-Li, or the corresponding organomagnesium compounds such as Grignard compounds, or organozinc compounds. On the one hand such metal alkyls transfer alkyl groups to the central metal, and on the other hand they trap water or catalyst poisons from the reaction medium or monomer during polymerization reactions. Metal alkyls of the type described can also advantageously be used in combination with aluminoxane cocatalysts, for instance to reduce the required amount of aluminoxane. Such anions are introduced when using e.g. the following boron compounds:

triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-diethylanilinium tetrakis(pentafluorophenyl)borate, N,N-diethylanilinium tetrakis(pentafluorophenyl)borate, N,N-dimethyl(2,4,5-trimethylanilinium) tetrakis(pentafluorophenyl)borate, trimethylammonium tetrakis(2,3,4,6-tetrafluorophenyl)borate, triethylammonium tetrakis(2,3,4,6-tetrafluorophenyl)borate, tripropylammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethylanilinium tetrakis(2,3,4,6-tetrafluorophenyl)borate, N,N-diethylanilinium tetrakis(2,3,4,6-tetrafluorophenyl) borate and N,N-dimethyl(2,4,6-trimethylanilinium) tetrakis (2,3,4,6-tetrafluorophenyl)borate; dialkylammonium salts such as: di(i-propyl)ammonium tetrakis(pentafluorophenyl) borate and dicyclohexylammonium tetrakis (pentafluorophenyl)borate; trisubstituted phosphonium salts such as: triphenylphosphonium tetrakis(pentafluorophenyl) borate, tri(o-tolyl)phosphonium tetrakis(pentafluorophenyl) borate and tri(2,6-dimethylphenyl)phosphonium tetrakis (pentafluorophenyl)borate; tritolylmethyl tetrakis (pentafluorophenyl)borate; triphenylmethyl tetraphenylborate (trityl tetraphenylborate); trityl tetrakis (pentafluorophenyl)borate; silver tetrafluoroborate; tris (pentafluorophenyl)borane; tris(trifluoromethyl)borane; and the corresponding organoaluminium compounds.

Further alternative possibilities are fluorinated but otherwise analogous boron and aluminium compounds having 1 to 3 fluorine substituents.

Other poorly coordinating anions can be formed from diboranyl or dialanyl compounds of the type

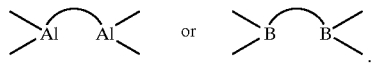

Activation by means of such bulky anions is effected for example by reacting the π complex compounds having a D/A bond with tris(pentafluorophenyl)borane, triphenylborane, triphenylaluminium, trityl tetrakis(pentafluorophenyl)borate or N,N-dialkylphenylammonium tetrakis(pentafluorophenyl)borate, as well as the corresponding alanes and alanates, or the corresponding phosphonium or sulfonium salts of borates, or alkali (alkaline earth) metal, thallium or silver salts of borates or alanates, carboranes, tosylates, triflates, perfluorocarboxylates, such as trifluoroacetate, or the corresponding acids. The π complex compounds of transition metals used are preferably those whose anion equivalents X are alkyl, allyl, aryl or benzyl groups. Such derivatives can also be prepared "in situ" by first reacting π complex compounds which have other anion equivalents X, such as F, Cl, Br, OR etc., with alkylaluminium compounds, organolithium compounds, Grignard compounds or alkylzinc or alkyllead compounds. The resulting reaction products can be activated with the above-mentioned boranes, borates, alanes or alanates without prior isolation.

It is also within the framework of the present invention simultaneously to use several π complex compounds having a D/A bond in order to produce a particular profile of material properties. Accordingly, it is also possible to use one or more π complex compounds having a D/A bond in combination with other π complex compounds which do not have a D/A bond.

The use according to the invention of the π complex compounds of transition metals with a D/A bond concerns the homopolymerization or copolymerization of monomers from the group comprising $C_2$–$C_{12}$-α-olefins, $C_4$–$C_{30}$-cycloolefins, $C_4$–$C_8$-diolefins, $C_2$–$C_8$-alkynes, $C_4$–$C_8$-vinyl esters and $C_8$–$C_{12}$-vinylaromatics.

Examples of said type are ethylene, propylene, 1-butene, 1-pentene, 1-hexene, 1-octene, 3-methyl-1-butene, 4-methyl-1-pentene, 4-methyl-1-hexene and (α-i-octene. Such olefins can also be substituted, for example by phenyl, substituted phenyl, halogen, an esterified carboxyl group or an acid anhydride group; this provides access to the group comprising said vinylaromatics and vinyl esters and other olefinically unsaturated compounds, for example styrene, methylstyrene, chlorostyrene, fluorostyrene, 4-vinylbiphenyl, vinylfluorene, vinylanthracene, methyl methacrylate, ethyl acrylate, vinylsilane, trimethylallylsilane, vinyl chloride, vinylidene chloride, tetrafluoroethylene, vinylcarbazole, vinylpyrrolidine, vinyl ethers and vinyl esters such as vinyl acetate or vinyl propionate. Preferred monomers are ethylene, propylene, butene, hexene, octene and methyl methacrylate.

Cyclic monomers are monocyclic or polycyclic and are covered by one of the two formulae below:

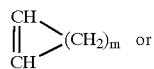
(XVI)

(XVII)

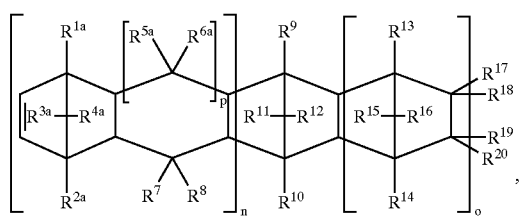

in which the subscripts are defined as follows:

m is a number from 2 to 10, preferably 3 to 6, n is the number 0 or 1, o is the number 0, 1, 2 or 3 and p is the number 0 or 1, in formula (XVI) two adjacent $CH_2$ groups can be replaced with the group —CH=CH—, and in formula (XVII) the radicals $R^{1a}$ to $R^{6a}$ and $R^7$ to $R^{20}$ independently of one another are hydrogen, fluorine, chlorine, bromine, linear or branched $C_1$–$C_{20}$-alkyl, $C_3$–$C_8$-cycloalkyl or $C_6$–$C_{16}$-aryl, it additionally being possible for the pair of radicals $R^{18}/R^{19}$ to be a double bond or one of the groups —$CHR^{21}$—$CHR^{22}$—$CHR^{23}$, —$CHR^{21}$—$CHR^{22}$—$CHR^{23}$—$CHR^{24}$— or —$CHR^{21}$—$CHR^{22}$—$CHR^{23}$—$CHR^{24}$—$CHR^{25}$—, in which $R^{21}$ to $R^{25}$ are hydrogen or $C_1$–$C_4$-alkyl, and it being possible for the pair of radicals $R^{17}/R^{18}$ to be the double-bonded group =C($R^{26}$,$R^{27}$), in which $R^{26}$ and $R^{27}$ are $C_1$–$C_4$-alkyl and $R^{27}$ can also be hydrogen.

Such cyclic monomers have one or more double bonds, preferably one or two double bonds, and are known; they are used for example in the processes of EP-A 610 852, EP-A 690 078 and U.S. Pat. No. 5,567,777.

Preferred cyclic monomers of formula (XVII) are those of the formulae

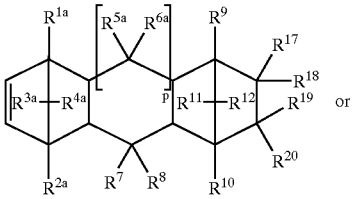
(XVIIa)

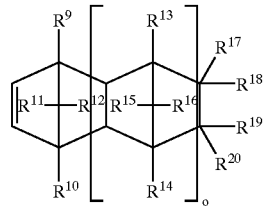
(XVIIb)

A non-exhaustive list of examples of such cyclic comonomers includes cyclobutene, cyclopentene, cyclopentadiene, cyclohexene, cycloheptene, cyclooctene, cyclodecene, cyclododecene, bicyclo-2-heptenes, tricyclo-3-decenes, tricyclo-3-undecenes, tetracyclo-3-dodecenes, pentacyclo-4-pentadecenes, pentacyclopentadecadienes, pentacyclo-3-pentadecenes, pentacyclo-4-hexadecenes, pentacyclo-3-hexadecenes, hexacyclo-4-heptadecenes, heptacyclo-5-eicosenes, heptacyclo-4-eicosenes, heptacyclo-5-heneicosenes, octacyclo-5-docosenes, nonacyclo-5-pentacosenes, nonacyclo-6-hexacosenes, cyclopentadiene/acenaphthylene adducts, 1,4-methano-1,4,4a,9a-tetrahydrofluorenes and 1,4-methano-1,4,4a,5,10,10a-hexahydroanthracenes, e.g. bicyclo[2.2.1]hept-2-ene (norbornene), norbornadiene, 5-methylnorbornene, 6-methylnorbornene, 5,6-dimethylnorbornene, 1-methylnorbornene, 5-isobutylnorbornene, 7-methylnorbornene, tricyclo[4.3.0.1$^{2,5}$]-3-decene (5,6-trimethylenenorbornene), tricyclo[4.4.0.1$^{2,5}$]-3-undecene (5,6-tetramethylenenorbornene), 10-methyltricyclo[4.4.0.1$^{2,5}$]-3-undecene, 6-ethylbicyclo[2.2.1]hept-2-ene, 6-n-butylbicyclo[2.2.1]hept-2-ene, 6-isobutylbicyclo[2.2.1]hept-2-ene, 2-methyltricyclo[4.3.0.1$^{2,5}$]-3-decene, 5-methyltricyclo[4.3.0.1$^{2,5}$]-3-decene, tricyclo[4.3.0.1$^{2,5}$]-3-undecene, tricyclo[4.3.0.1$^{2,5}$]-3,7-decadiene (dicyclopentadiene), tricyclo[4.3.0.1$^{2,5}$]-3-decene, tetracyclo[4.4.0.1$^{2,5}$.1$^{7,10}$]-3-dodecene, 8-methyltetracyclo [4.4.0.1$^{2,5}$.1$^{7,10}$]-3-dodecene, 8-cyclohexyltetracyclo [4.4.0.1$^{2,5}$.1$^{7,10}$]-3-dodecene, 8-stearyltetracyclo[4.4.0.1$^{2,5}$.1$^{7,10}$]-3-dodecene, the 5,10-dimethyl, 2,10-dimethyl, 8,9-dimethyl, 11,12-dimethyl, 2,7,9-trimethyl, 9-isobutyl, 11,12-dimethyl, 8-ethylidene-9-methyl, 8-chloro, 8-bromo or 8-fluoro derivative of tetracyclo[4.4.0.1$^{2,5}$.1$^{7,10}$]-3-dodecene, 8-methyltetracyclo[4.4.0.1$^{2,5}$.1$^{7,10}$]-3-dodecene, 8-propyltetracyclo[4.4.0.1$^{2,5}$.1$^{7,10}$]-3-dodecene, 8-butyltetracyclo[4.4.0.1$^{2,5}$.1$^{7,10}$]-3-dodecene, 8-isobutyltetracyclo[4.4.0.1$^{2,5}$.1$^{7,10}$]-3-dodecene, 8-hexyltetracyclo[4.4.0.1$^{2,5}$.1$^{7,10}$]-3-dodecene, 8-methyl-9-ethyltetracyclo[4.4.0.1$^{2,5}$.1$^{7,10}$]-3-dodecene, 9-ethyl-2,7-dimethyltetracyclo[4.4.0.1$^{2,5}$.1$^{7,10}$]-3-dodecene, 9-isobutyl-2,7-dimethyltetracyclo[4.4.0.1$^{2,5}$.1$^{7,10}$]-3-dodecene, 9,11,12-trimethyltetracyclo[4.4.0.1$^{2,5}$.1$^{7,10}$]-3-dodecene, 9-ethyl-11,12-dimethyltetracyclo[4.4.0.1$^{2,5}$.1$^{7,10}$]-3-dodecene, 9-isobutyl-11,12-dimethyltetracyclo[4.4.0.1$^{2,5}$.1$^{7,10}$]-3-dodecene, 5,8,9,10-tetramethyltetracyclo[4.4.0.1$^{2,5}$.1$^{7,10}$]-3-dodecene, 8-ethylidenetetracyclo[4.4.0.1$^{2,5}$.1$^{7,10}$]-3-dodecene, 8-ethylidene-9-methyltetracyclo[4.4.0.1$^{2,5}$.1$^{7,10}$]-3-dodecene, 8-ethylidene-9-ethyltetracyclo[4.4.0.1$^{2,5}$.1$^{7,10}$]-3-dodecene, 8-ethylidene-9-isopropyltetracyclo[4.4.0.1$^{2,5}$.1$^{7,10}$]-3-dodecene, 8-ethylidene-8-butyltetracyclo[4.4.0.1$^{2,5}$.1$^{7,10}$]-3-dodecene, 8-n-propylidenetetracyclo[4.4.0.1$^{2,5}$.1$^{7,10}$]-3-dodecene, 8-n-propylidene-9-methyltetracyclo[4.4.0.1$^{2,5}$.1$^{7,10}$]-3-dodecene, 8-n-propylidene-9-ethyltetracyclo[4.4.0.1$^{2,5}$.1$^{7,10}$]-3-dodecene, 8-n-propylidene-9-isopropyltetracyclo[4.4.0.1$^{2,5}$.1$^{7,10}$]-3-dodecene, 8-n-propylidene-9-butyltetracyclo[4.4.0.1$^{2,5}$.1$^{7,10}$]-3-dodecene, 8-isopropylidenetetracyclo[4.4.0.1$^{2,5}$.1$^{7,10}$]-3-dodecene, 8-isopropylidene-9-methyltetracyclo[4.4.0.1$^{2,5}$.1$^{7,10}$]-3-dodecene, 8-isopropylidene-9-ethyltetracyclo[4.4.0.1$^{2,5}$.1$^{7,10}$]-3-dodecene, 8-isopropylidene-9-isopropyltetracyclo[4.4.0.1$^{2,5}$.1$^{7,10}$]-3-dodecene, 8-isopropylidene-9-butyltetracyclo[4.4.0.1$^{2,5}$.1$^{7,10}$]-3-dodecene, 8,9-dichlorotetracyclo[4.4.0.1$^{2,5}$.1$^{7,10}$]-3-dodecene, pentacyclo[6.5.1.1$^{3,6}$.0$^{2,7}$.0$^{9,13}$]-4-pentadecene, pentacyclo[7.4.0.1$^{2,5}$.1$^{9,12}$.0$^{8,13}$]-3-pentadecene, pentacyclo[8.4.0.1$^{2,5}$.1$^{9,12}$.0$^{8,13}$]-3-hexadecene, 1,3-dimethylpentacyclo[6.5.1.1$^{3,6}$.0$^{2,7}$.0$^{9,13}$]-4-pentadecene, 1,6-dimethyl[6.5.1.1$^{3,6}$.0$^{2,7}$.0$^{9,13}$]-4-pentadecene, 14,15-dimethyl[6.5.1.1$^{3,6}$.0$^{2,7}$.0$^{9,13}$]-4-pentadecene, pentacyclo[7.4.0.1$^{2,5}$.1$^{9,12}$.0$^{8,13}$]-3-pentadecene, methyl-substituted pentacyclo[7.4.0.1$^{2,5}$.1$^{9,12}$.0$^{8,13}$]-3-pentadecene, pentacyclo[6.5.1.1$^{3,6}$.0$^{2,7}$.0$^{9,13}$]-4,10-pentadecadiene, 11-methylpentacyclo[8.4.0.1$^{2,5}$.1$^{9,12}$.0$^{8,13}$]-3-hexadecene, 11-ethyl[8.4.0.1$^{2,5}$.1$^{9,12}$.0$^{8,13}$]-3-hexadecene, 10,11-dimethyl[8.4.0.1$^{2,5}$.1$^{9,12}$.0$^{8,13}$]-3-hexadecene, pentacyclo[6.6.1.1$^{3,6}$.0$^{2,7}$.0$^{9,14}$]-hexadecene, 1,3-dimethylpentacyclo[6.6.1.1$^{3,6}$.0$^{2,7}$.0$^{9,14}$]-4-hexadecene, 15,16-dimethylpentacyclo[6.6.1.1$^{3,6}$.0$^{2,7}$.0$^{9,14}$]-4-hexadecene, hexacyclo[6.6.1.1$^{3,6}$.1$^{10,13}$.0$^{2,7}$.0$^{9,14}$]heptadecene, heptacyclo[8.7.0.1$^{2,9}$.1$^{4,7}$.1$^{11,17}$.0$^{12,16}$]-5-eicosene, heptacyclo[8.8.0.1$^{4,7}$.1$^{11,18}$.1$^{13,16}$.0$^{3,8}$.0$^{12,17}$]-5-heneicosene, 12-methylhexacyclo[6.6.1.1$^{3,6}$.1$^{10,13}$.0$^{2,7}$.0$^{9,14}$]-4-heptadecene, 12-ethylhexacyclo[6.6.1.1$^{3,6}$.1$^{10,13}$.0$^{2,7}$.0$^{9,14}$]-4-heptadecene, 12-isobutylhexacyclo[6.6.1.1$^{3,6}$.1$^{10,13}$.0$^{2,7}$.0$^{9,14}$]-4-heptadecene, 1,6,10-trirethylhexacyclo[6.6.1.1$^{3,6}$.1$^{10,13}$.0$^{2,7}$.0$^{9,14}$]-4-heptadecene, heptacyclo[8.7.0.1$^{3,6}$.1$^{10,17}$.1$^{12,15}$.0$^{2,7}$.0$^{11,16}$]-4-eicosene and its dimethyl-substituted derivatives, heptacyclo[8.8.0.1$^{4,7}$.1$^{11,18}$.1$^{13,16}$.0$^{3,8}$.0$^{12,17}$]-5-heneicosene and its trimethyl-substituted derivatives, 15-methylheptacyclo[8.8.0.1$^{4,7}$.1$^{11,18}$.1$^{13,16}$.0$^{3,8}$.0$^{12,17}$]-5-heneicosene, 5-phenylbicyclo[2.2.1]hept-2-ene, 5-methyl-5-phenylbicyclo[2.2.1]hept-2-ene, 5-benzylbicyclo[2.2.1]hept-2-ene, 5-tolylbicyclo[2.2.1]hept-2-ene, 2-(ethylphenyl)bicyclo[2.2.1]hept-2-ene, 5-(isopropylphenyl)bicyclo[2.2.1]hept-2-ene, 5-biphenylbicyclo[2.2.1]hept-2-ene, 5-(β-naphthyl)bicyclo[2.2.1]hept-2-ene, 5-(α-naphthyl)bicyclo[2.2.1]hept-2-ene, 5-(anthracenyl)bicyclo[2.2.1]hept-2-ene, 5,6-diphenylbicyclo[2.2.1]hept-2-ene, 1,4-methano-1,4,4a,9a-tetrahydrofluorene, 1,4-methano-1,4,4a,5,10,10a-hexahydroanthracene, 8-phenyltetracyclo[4.4.0.1$^{2,5}$.1$^{7,10}$]-3-dodecene, 8-methyl-8-phenyltetracyclo[4.4.0.1$^{2,5}$.1$^{7,10}$]-3-dodecene, 8-benzyltetracyclo[4.4.0.1$^{2,5}$.1$^{7,10}$]-3-dodecene, 8-tolyltetracyclo[4.4.0.1$^{2,5}$.1$^{7,10}$]-3-dodecene, 8-(ethylphenyl)tetracyclo[4.4.0.1$^{2,5}$.1$^{7,10}$]-3-dodecene, 8-(isopropylphenyl)tetracyclo[4.4.0.1$^{2,5}$.1$^{7,10}$]-3-dodecene, 8,9-diphenyltetracyclo[4.4.0.1$^{2,5}$.1$^{7,10}$]-3-dodecene, 8-(biphenyl)tetracyclo[4.4.0.1$^{2,5}$.1$^{7,10}$]-3-dodecene, 8-(β-naphthyl)tetracyclo[4.4.0.1$^{2,5}$.1$^{7,10}$]-3-dodecene, 8-(α-naphthyl)tetracyclo[4.4.0.1$^{2,5}$.1$^{7,10}$]-3-dodecene, and 8-(anthracenyl)tetracyclo[4.4.0.1$^{2,5}$.1$^{7,10}$]-3-dodecene.

The homopolymerizations or copolymerizations to be carried out with the π complex compounds according to the invention are performed under adiabatic or isothermal conditions. This entails high-pressure processes in autoclaves or tubular reactors, solution or high-temperature solution processes, bulk polymerization processes, slurry phase polymerization processes in stirred reactors or loop reactors, and gas phase processes, the pressures for the slurry, solution and gas phases generally not exceeding 65 bar. All these processes have been known as such for a long time and are familiar to those skilled in the art. It is an advantage of the π complex compounds according to the invention that, by choosing the substituents, they can be prepared either as soluble π complex compounds, optionally applied to supports, or as insoluble heterogeneous π complex compounds.

Examples of polymers which can be prepared with the π complex compounds according to the invention are linear high density polyethylene (HDPE), isotactic polypropylene (iPP), syndiotactic polypropylene (sPP), syndiotactic polystyrene, i- or s-polybutene or -polyhexene, polyoctene, polybutadiene, linear low density copolymer, e.g. ethylene with $C_3$–$C_{20}$-α-olefin (linear low density polyethylene, LLDPE), for example ethylene/propylene, ethylene/butylene, ethylene/hexene and ethylene/octene, and also, for instance, propylene/butylene, propylene/hexene, ethylene/styrene, propylene/styrene, 1,3-butadiene/ethylene, 1,3-butadiene/styrene, the analogous isoprene copolymers etc. Possible examples of readily obtainable terpolymers are ethylene/propylene/ethylidenenorbornene (ENB), ethylene/propylene/dicyclopentadiene, ethylene/propylene/vinylnorbornene and ethylene/propylene/7-methyloctadiene.

Through the donor-acceptor bridge, the π complex compounds to be used according to the invention allow a definite opening of the active centre, particularly also for sterically demanding monomers, thereby ensuring not only a high activity but also a controlled selectivity, a controlled molecular weight distribution and a uniform incorporation of (co)monomers. A high uniformity of the molecular weight distribution is also a consequence of the uniform and definite site of the polymerization effected by insertion (single site catalyst). Furthermore, the π complex compounds according to the invention make it possible to obtain products with long branched chains in the polymerization process, which have the effect of improving the rheology.

The D/A bond can stabilize the catalysts right up to high temperatures, so the catalysts can also be employed in the high temperature range.

EXAMPLES

All the reactions were carried out under strictly anaerobic conditions using Schlenk techniques or the high-vacuum technique. The solvents used were dry and saturated with argon. Chemical shifts δ are given in ppm relative to the appropriate standard: $^1$H (tetramethylsilane), $^{13}$C (tetramethylsilane), $^{31}$P (85% $H_3PO_4$), $^{11}$B (boron trifluoride etherate: −18.1 ppm). Minus signs signify a shift to higher field.

Example 1

Bis(trimethylsilyl)cyclopentadiene, compound 1

14.7 g (0.106 moles) of trimethylsilylcyclopentadiene (obtained from Fluka) and 150 ml of tetrahydrofuran (THF) were placed in a reaction flask and cooled to 0° C. 47.4 ml of a solution of butyllithium in n-hexane (2.3 molar; total amount 0.109 moles) were added dropwise over 20 minutes. When the addition was complete, the yellow solution was stirred for a further one hour and the cooling bath was then removed. At room temperature the solution was stirred for a further one hour and then cooled to −20° C. 14.8 ml (0.117 moles) of trimethylsilyl chloride were then added dropwise over 10 minutes and the reaction mixture was stirred for two hours at −10° C. The cooling bath was then removed and the reaction solution was heated to room temperature and subsequently stirred for a further one hour. The reaction mixture was filtered through Celite; the filter was washed with hexane and the hexane was removed from the combined filtrates under vacuum. On distillation at 26° C. under 0.4 mbar, the crude product gave 19 g of pure compound 1 (85% of the theoretical yield). Boiling point and NMR data are consistent with the literature (J. Organometallic Chem. 29, (1971), 227; ibid. 30, (1971), C 57; J. Am. Chem. Soc. 102, (1980), 4429; J. Gen. Chem. USSR, Eng. Transl. 43, (1973), 1970; J. Chem. Soc., Dalton Trans. 1980, 1156). $^1$H NMR (400 MHz, $C_6D_6$): δ=6.74 (m, 2H); 6.43 (m, 2H); −0.04 (s, 18H).

Example 2

Diphenylphosphinocyclopentadienyllithium, compound 3

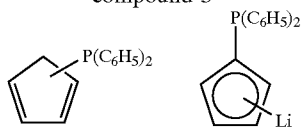

50 g (0.186 moles) of cyclopentadienylthallium (obtained from Fluka) were placed in a 500 ml flask together with 300 ml of diethyl ether. The suspension was cooled to 0° C. and 34.2 ml (0.186 moles) of diphenylchlorophosphine were added dropwise over 10 minutes. The suspension was then heated to room temperature, stirred for one hour and finally filtered through a frit. The solvent was then stripped off under vacuum to leave 39.5 g (85% of the theoretical yield) of the intermediate diphenylphosphinocyclopentadiene, compound 2. An 18.6 g portion (0.074 moles) of compound 2 was then diluted with toluene and cooled to 0° C. 33.2 ml of a 2.24 molar solution of butyllithium in hexane (0.074 moles) were added to this solution over 10 minutes. After being heated to room temperature and stirred for 2 hours, the yellow solution produced a precipitate, which was filtered off and washed with toluene and then with hexane. After drying under vacuum, 13.2 g of compound 3 (70% of the theoretical yield) were obtained in the form of a brownish powder (cf. J. Am. Chem. Soc. 105, (1983), 3882; Organometallics 1, (1982), 1591). $^1$H NMR (400 MHz, THF-$d_8$): δ=7.3 (m, 4H); 7.15 (m, 6H); 5.96 (m, 2H); 5.92 (m, 2H); $^{31}$P NMR (161.9 MHz, THF-$d_8$): δ=−20.

Example 3

Tributylstannyldiphenylphosphinoindene, compound 4

10 g (0.086 moles) of indene were placed in a round-bottomed flask, diluted with 200 ml of diethyl ether and cooled to −20° C. 36 ml of a 2.36 molar solution of butyllithium (0.085 moles) in n-hexane were added to this solution, which immediately assumed a yellow colouration. The cooling bath was removed and the reaction mixture was allowed to warm up to room temperature and stirred for a further one hour. The reaction mixture was then cooled to 0° C. again and 19 g (15.9 ml, 0.086 moles) of diphenylchlorophosphine were added to form a precipitate. The cooling bath was removed again and the solution was able to warm up to room temperature, stirring being continued for a further one hour. The solution was then cooled to −20° C. again and 36 ml (0.085 moles) of butyllithium in n-hexane were added dropwise. When the addition was complete, the cooling bath was removed again and the temperature rose to room temperature; the solution was stirred for a further 1.5 hours. The suspension was then cooled to 0° C. again and 28 g (0.086 moles) of tributyltin chloride were added dropwise. The resulting suspension was heated to room temperature and stirred for a further 1.5 hours; it was then filtered through a frit and the solvent was removed under vacuum to leave 46.9 g of compound 4 (92% of the theoretical yield) in the form of a heavy yellow oil. $^1$H NMR (400 MHz, $CDCl_3$): δ=7.5–7.3 (m, 6H); 7.28 (bs, 6H); 7.14 (pseudo dt, 7.3 Hz/1.0 Hz, 1H); 7.08 (t, J=7.3 Hz, 1H); 6.5 (bm, 1H); 4.24 (bs, 1H); 1.4–1.25 (m, 6H); 1.25–1.15 (m, 6H); 0.82 (t, J 7.2 Hz, 9H); 0.53 (t, J=8 Hz, 6H); $^-$P NMR (161.9 MHz, $CDCl_3$): δ=−20.6.

Example 4

Diphenylphosphinoindenylzirconium trichloride, compound 5

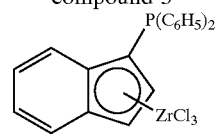

A solution of 37 g (0.0628 moles) of compound 4 in 300 ml of toluene was added over 3 hours to a suspension of 14.6 g of $ZrCl_4$ (99.9% pure, 0.0628 mole, obtained from Aldrich) in 100 ml of toluene at room temperature. The solution immediately became red and slowly turned orange and ultimately yellow. After stirring for 4 hours, the yellow precipitate was filtered off and washed with toluene and then with hexane. The solid was dried under vacuum to give 15.3 g (50% of the theoretical yield) of compound 5 in the form of a free-flowing yellow powder. The yield could easily be increased to over 70% by working at a lower temperature, e.g. 30 min at −30° C. and 5 hours at 0° C. The product could be purified further by washing out residual tin compound using pentane in a Soxhlet extractor (extraction time: 8 hours).

Example 5

N,N-Dimethyl-O-(methylsulfonyl)hydroxylamine, compound 6

$(CH_3)_2NOSO_2CH_3$      6

9.0 g of N,N-dimethyl-O-hydroxylamine hydrochloride (0.092 moles) were suspended in 70 ml of $CH_2Cl_2$ contain ing 20 g of triethylamine (0.2 moles), and the suspension was cooled to −10° C. 9.5 g of methylsulfonyl chloride (0.083 moles) dissolved in 70 ml of $CH_2Cl_2$ were slowly added dropwise to the cooled suspension. When the addition was complete, the reaction mixture was stirred for 1 h. Ice-water was then added and the organic phase was separated off. The water left behind was washed with ether. The wash ether and $CH_2Cl_2$ fraction were combined and dried over $Na_2SO_4$ and the solvents were removed under vacuum at −10° C. to leave 5.9 g (46% of the theoretical yield) of compound 6 in the form of an oil, which was stored at −20° C.; cf. Angew. Chem., Int. Ed. Engl. 17, (1978), 687. $^1$H NMR (400 MHz, $CDCl_3$): δ=3.03 (s, 3H); 2.84 (s, 6H).

Example 6

N,N-Dimethylaminocyclopentadienyllithium, compound 7

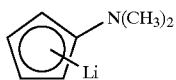

7

A solution of 3 g of cyclopentadienyllithium (0.042 moles) in 30 ml of THF was added slowly at −30° C. to a solution of 5.9 g of compound 6 (0.042 moles) in 20 ml of THF. The mixture was then heated to −20° C. and stirred for 30 min. Hexane was then added and the solution was filtered. 1.8 ml of a 2.3 molar solution of butyllithium (0.042 moles) in hexane were then added at −20° C. to produce a precipitate. The precipitate was filtered off and washed with twice 20 ml of hexane. After drying under vacuum, 2.0 g (40% of the theoretical yield) of compound 7 were obtained in the form of a white powder; cf. Angew. Chem., Int. Ed. Engl. 19, (1980), 1010. $^1$H NMR (400 MHz, THF): δ=5.34 (bd, J=2.2 Hz, 2H); 5.15 (bd, J 2.2 Hz, 2H); 2.56 (s, 6H).

Example 7

Tributylstannyldiisopropylphosphinoindene, compound 8

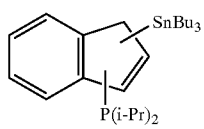

8

100 ml of ether were placed in a round-bottomed flask containing 3.8 g (0.033 moles) of indene and the solution was cooled to −20° C. 14.4 ml of a 2.3 molar solution of butyllithium in hexane (0.033 moles) were added over 5 minutes to form a yellow solution. After removal of the cooling bath, the solution was heated to room temperature and subsequently stirred for 1.5 h. The reaction mixture was then cooled to 0° C. and 5.0 g of chlorodiisopropylphosphine (0.033 moles) were added to form a precipitate. After removal of the cooling bath, the solution was heated to room temperature and stirred for 1 h. The solution was then cooled to −20° C. and 14.4 ml of a 2.3 molar solution of butyllithium in hexane (0.033 moles) were added dropwise. When the addition was complete, the cooling bath was removed and the solution was heated slowly to room temperature and stirred for 1.5 h. After cooling of the suspension to 0° C., 10.1 g of chlorotributyltin (0.031 moles) were added dropwise. The suspension formed was heated to room temperature and stirred for 1.5 h. The ether was removed under vacuum, the crude product was dissolved in hexane again, the solution was filtered and the filtrate was concentrated to dryness under vacuum to leave 16.6 g of compound 8 (yield: 97%) in the form of a heavy yellow oil. Two isomers were obtained in proportions of 1.5:1. The main isomer was identified as follows: $^1$H NMR (400 MHz, $CD_2Cl_2$): δ=7.71 (d, J=7.2 Hz, 1H); 7.41 (d, J=7.3 Hz, 1H); 7.13 (m, 2H); 6.96 (m, 1H); 4.28 (s with Sn satellites, 1H); 2.21 (m, 1H); 1.54 (m, 1H); 1.45–0.65 (m, 39H); $^{31}$P NMR (161.9 MHz, $CD_2Cl_2$): δ=−11.3 ppm. The secondary isomer was identified as follows: $^1$H NMR (400 MHz, $CD_2Cl_2$): δ=7.6 (d, J=7.4 Hz, 1H); 7.46 (d, J=7.2 Hz, 1H); 7.26 (t, J=7.5 Hz, 1H); 7.1 (m, 1H); 6.71 (m, 1H); 3.48 (m, 1H); 2.21 (m, 1H); 1.54 (m, 1H); 1.45–0.65 (m, 39H); $^{31}$P NMR (161.9 MHz, $CD_2Cl_2$): d=−1.5 ppm.

Example 8

Diisopropylphosphinoindenylzirconium trichloride, compound 9

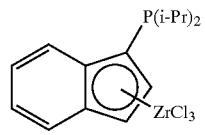

9

A solution of 15.0 g of compound 8 (0.029 moles) in 50 ml of toluene was added to a suspension of 6.7 g (0.029 moles) of 99.9% pure $ZrCl_4$ in 300 ml of toluene at −78° C. When the addition was complete, the reaction mixture was stirred for 0.5 h at −30° C. and then for 4 h at 0° C. The yellow precipitate formed was filtered off and washed with toluene and hexane. The solids were dried under vacuum to leave 8.8 g of compound 9 (yield: 71%) in the form of a free-flowing yellow powder. The powder was purified further by removal of the residual tin compounds by means of extraction with refluxing toluene over a period of 3 h at 30 mm Hg and then with pentane over a period of 2 h in a Soxhlet extractor. No $^1$H NMR was obtained because of the insolubility of the compound formed.

Example 9

Tributylstannyldimethylphosphinoindene, compound 10

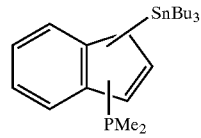

10

150 ml of ether were placed in a round-bottomed flask containing 5.5 g (0. 047 moles) of indene; the solution was cooled to −20° C. 20.8 ml of a 2.3 molar solution of butyllithium in hexane (0.048 moles) were added over 5 min to form a yellow solution. After removal of the cooling bath, the solution was heated to room temperature and subsequently stirred for 1 h. After cooling of the reaction mixture to −30° C., 4.6 g of chlorodimethylphosphine (0.048 moles) in 30 ml of ether were added over 20 min to form a precipitate. After stirring for 2 hours at −20° C., 20.8 ml of a 2.3 molar solution of butyllithium in hexane (0.048 moles) were added dropwise. When the addition was complete, the cooling bath was removed and the solution was heated slowly to room temperature and stirred for 1.5 h. After cooling of the suspension to 0° C., 15.6 g of chlorotributyltin (0.048 moles) were added dropwise. The suspension formed was heated to room temperature and stirred for 1.5 h. The ether was removed under vacuum, the crude product was dissolved in hexane again, the solution was filtered and the filtrate was concentrated to dryness under vacuum to leave 17.4 g of compound 10 (yield: 78%) in the form of a heavy yellow oil. $^1$H NMR (400 MHz, CD$_2$Cl$_2$): δ=7.67 (d, J=7.5 Hz, 1H); 7.47 (d, J=7.4 Hz, 1H); 7.18 (m, 2H); 6.83 (m, 1H); 4.28 (s with Sn satellites, 1H); 1.43–0.78 (m, 33H); $^3$P NMR (161.9 MHz, CD$_2$Cl$_2$): δ=−61.6 ppm.

Example 10

Dimethylphosphinoindenylzirconium trichloride, compound 11

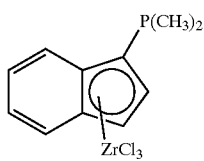

A solution of 17.0 g of compound 10 (0.037 moles) in 50 ml of toluene was added to a suspension of 8.5 g (0.036 moles) of 99.9% pure ZrCl$_4$ in 200 ml of toluene at −78° C. When the addition was complete, the reaction mixture was stirred for 0.5 h at −30° C. and then for 4 h at 0° C. The yellow precipitate formed was filtered off and washed with toluene and hexane. The solids were dried under vacuum to leave 8.3 g of compound 11 (yield: 61%) in the form of a free-flowing yellow powder. The powder was purified further by removal of the residual tin compounds by means of extraction with refluxing toluene over a period of 3 h at 30 mm Hg and then with pentane over a period of 2 h in a Soxhlet extractor to leave 7.2 g (yield: 53%) of product. No $^1$H NMR was obtained because of the insolubility of this compound.

Example 11

2-Methylindene, compound 13

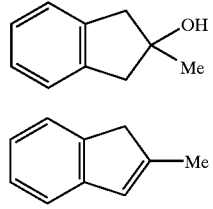

38.7 g (0.29 moles) of 2-indanone and 300 ml of ether were placed in a round-bottomed flask. 96.7 ml of a 3.0 molar solution of CH$_3$MgI in ether (0.29 moles), diluted with 150 ml of ether, were placed in a second flask. The 2-indanone solution was then added to the CH$_3$MgI solution through a small tube in an amount such that reflux was maintained; a precipitate was formed. When the addition was complete, the suspension was stirred for a further 4 h under reflux and cooled to 0° C., after which 100 ml of a saturated solution of NH$_4$Cl were added slowly. The product was extracted with ether and dried over MgSO$_4$. After removal of the solvent under vacuum, 30.1 g (yield: 70%) of 2-methyl-2-indanol (compound 12) were obtained in the form of an oily solid. $^1$H NMR (400 MHz, CDCl$_3$): δ=7.15 (bm, 4H); 3.01 (s, 2H); 2.99 (s, 2H); 1.5 (s, 3H); OH variable.

25.5 g (0.17 moles) of compound 12, 3.2 g (0.017 moles) of p-toluenesulfonic acid and 500 ml of hexane were placed in a round-bottomed flask fitted with a Dean-Stark apparatus. This suspension was refluxed for 3 h. After cooling, the hexane fraction was decanted from the insoluble products and the solvent was removed under vacuum to leave an oil, which was then distilled in a short distillation column at 45° C. and 0.03 mbar to give 15 g (yield: 68%) of compound 13. $^1$H NMR (400 MHz, CDCl$_3$): δ=7.33 (d, J=7.6 Hz. 1H); 7.21 (m, 2H); 7.06 pseudo dt, J=7.2, 1.4 Hz, 1H); 6.45 (bs, 1H); 3.25 (s, 2H); 2.12 (s, 3H).

Reference is made to the following publications:

1. Morrison, H.; Giacherio, D. *J. Org. Chem.* 1982, 47, 1058.
2. Ready, T. E.; Chien, J. C. W.; Rausch, M. D. *J. Organom. Chem.* 519, 1996, 21.
3. Wilt, Pawlikowki, Wieczorek *J. Org. Chem.* 37, 1972, 824.

Example 12

Tributylstannyldiisopropylphosphino-2-methylindene, compound 14

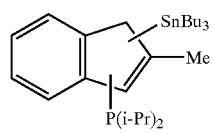

150 ml of ether were placed in a round-bottomed flask containing 5.08 g (0.039 moles) of 2-methylindene 13; the solution was cooled to −20° C. 17.0 ml of a 2.3 molar solution of butyllithium in hexane (0.039 moles) were added over 5 min to form a yellow solution. After removal of the cooling bath, the solution was heated to room temperature and subsequently stirred for 1 h. The reaction mixture was then cooled to −20° C. and 5.8 g (0.039 moles) of chlorodiisopropylphosphine were added over 5 min to form a precipitate. The cooling bath was then removed and the reaction mixture was stirred for 1 h at room temperature. After cooling to −20° C., 17.0 ml of a 2.3 molar solution of butyllithium in hexane (0.039 moles) were added dropwise. When the addition was complete, the cooling bath was removed and the solution was heated slowly to room temperature and stirred for 1.5 h. After cooling of the suspension to 0° C., 12.4 g (0.038 moles) of chlorotributyltin were added dropwise. The suspension formed was heated to room temperature and stirred for 1.5 h. The ether was removed under vacuum, the crude product was dissolved in hexane again, the solution was filtered and the filtrate was concentrated to dryness under vacuum to leave 20.4 g (yield: 98%) of compound 14 in the form of a heavy yellow oil. Two isomers were identified by $^{31}$P NMR. $^{31}$P NMR (161.9 MHz, CD$_2$Cl$_2$): δ=−5.9 and −6.6 in a ratio of 2:1.

Example 13

Diisopropylphosphino-2-methylindenylzirconium trichloride, compound 15

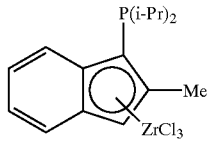

A solution of 17.7 g (0.033 moles) of compound 14 in 100 ml of methylene chloride was added over 10 min at −25° C. to a suspension of 7.7 g (0.033 moles) of 99.9% pure $ZrCl_4$ in 200 ml of methylene chloride. When the addition was complete, the reaction mixture was heated slowly to 10° C. over a period of 3 h to form a clear orange-coloured solution. After 1 h at room temperature, the solvent was removed under vacuum and the oil formed was washed with 2×50 ml of hexane to give an oily crude product (15), which was further processed directly. No $^1$H NMR was obtained because of the insolubility of this compound.

Example 14

Bis(trimethylsilyl)(diphenylphosphino) cyclopentadiene, compound 16

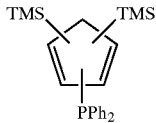

TMS = ——Si(CH$_3$)$_3$ 76.6 ml of a 2.5 molar solution of butyllithium in hexane (0.19 moles) were added over 10 min at 0° C. to a solution of compound 1 (40.2 g, 0.19 moles) in 500 ml of ether. When the addition was complete. the bath was removed and the solution was stirred for 1 h at room temperature. After cooling to 0° C., 42.2 g (0.19 moles) of chlorodiphenylphosphine were added over 10 min, after which the bath was removed and the suspension was heated to room temperature. After stirring for 1 hour at room temperature, the ether was removed under vacuum and the product was dissolved in hexane again. After the salts had been filtered off, the hexane was removed under vacuum to leave 69.1 g (yield: 91%) of compound 16 in the form of an oil. $^1$H NMR (400 MHz, CDCl$_3$): δ=7.45 (m, 4H); 7.35 (m, 6H); 6.8 (m, 1H); 6.65 (m, 1H); 6.6 (m, 1H); 0 (s, 18H); $^{31}$P NMR (161.9 MHz, CDCl$_3$): δ=−19.5 ppm.

Example 15

Trimethylsilyldiphenylphosphinocyclopentadienyl-zirconium trichloride, compound 17

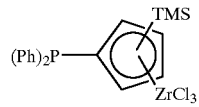

A solution of compound 16 (69.1 g, 0.175 moles) in 200 ml of methylene chloride was added through a small tube to a suspension of 41.5 g (0.178 moles) of 99.9% pure $ZrCl_4$ in 200 ml of methylene chloride and the mixture was stirred for 8 h at room temperature. The solution became turbid during this time. The solids were filtered off, washed with 2×20 ml of toluene and then with 2×20 ml of hexane and dried under vacuum. The product consisted of 35 g (yield: 39%) of a pale yellow powder. No $^1$H NMR was obtained because of the insolubility of the product.

Example 16

Diisopropylphosphinocyclopentadienyllithium, compound 18

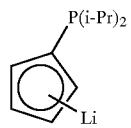

50 ml of ether were placed in a round-bottomed flask containing 1.68 g (0.023 moles) of cyclopentadienyllithium. After cooling of the reaction flask to −20° C., 3.6 g (0.023 moles) of chlorodiisopropylphosphine were added dropwise. When the addition was complete, the cooling bath was heated to 0° C. and the reaction mixture was stirred for 1 h. Ether was then removed under vacuum, the product was dissolved in toluene and the solution was filtered. After the frit had been rinsed with 2×10 ml of toluene, the reaction mixture was cooled to −20° C. and 9.3 ml of a 2.5 molar solution of butyllithium in hexane (0.023 moles) were added to form an orange coloured solution. A small fraction was taken for NMR studies and, after separation of the toluene under vacuum and washing of the resulting oil with hexane, a pale yellow solid (18) was obtained. $^1$H NMR (400 MHz, THF): δ=5.89 (m, 2H); 5.83 (bs, 2H); 1.86 (m, 2H); 1.0–0.8 (m, 12H).

Example 17

Dimethylphosphinotributylstannyl-2-methylindene, compound 19

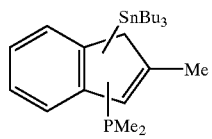

100 ml of ether were placed in a round-bottomed flask containing 6.76 a (0.052 moles) of 2-methylindene (compound 1); the solution was cooled to −20° C. 21 ml of a 2.5 molar solution of butyllithium in hexane (0.052 moles) were added over 5 min to form a yellow solution. After removal of the cooling bath, the solution was heated to room temperature and subsequently stirred for 1 hour. After cooling of the reaction mixture to −20° C., 5.0 g (0.052 moles) of chlorodimethylphosphine were added over 5 min to form a precipitate. The cooling bath was then removed and the reaction mixture was stirred for 1 h at room temperature. After cooling to −20° C., 21.0 ml of a 2.5 molar solution of butyllithium in hexane (0.052 moles) were added dropwise. When the addition was complete, the cooling bath was removed, after which the solution was heated slowly to room temperature and stirred for 1.5 h. After cooling of the suspension to 0° C., 16.9 g (0.052 moles) of chlorotributyltin were added dropwise. The suspension formed was heated to room temperature and stirred for 1.5 h. After removal of the ether under vacuum, the crude product was dissolved in hexane again, the solution was filtered and the filtrate was concentrated to dryness under vacuum to leave 24.3 g (yield: 98%) of compound 19 in the form of a heavy yellow oil. $^{31}$P NMR (161.9 MHz, CDCl$_2$): δ=−68.5 (s).

Example 18

Dimethylphosphino-2-methylindenylzirconium trichloride, compound 20

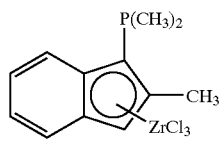

A solution of 17.4 g (0.036 moles) of compound 19 in 100 ml of toluene was added over 10 min at 0° C. to a suspension of 8.5 g (0.036 moles) of 99.9% pure ZrCl$_4$ in 100 ml of toluene. When the addition was complete, the reaction mixture was heated slowly to 10° C. over a period of 1 h and then stirred for 6 h at room temperature. The yellow precipitate was then filtered off, washed with 2×20 ml of toluene and 2×20 ml of hexane and dried under vacuum. The powder was purified further by removal of the residual tin compounds by means of extraction with refluxing toluene over a period of 3 h at 30 mm Hg and then with pentane over a period of 2 h in a Soxhlet extractor to leave 5.8 g (yield: 41%) of compound 20 in the form of a bright yellow powder. No $^1$H NMR was obtained because of the insolubility of this compound.

Example 19

4,7-Dimethylindene, compound 21

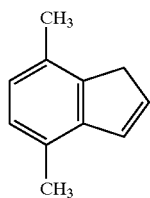

Reference is made to: Erker, G. et al. *Tetrahedron* 1995, 51, 4347.

A 30% solution of 153 g (2.8 moles) of sodium methoxide in methanol was diluted with 60 ml of methanol and cooled to 0° C. 34 g (0.52 moles) of cyclopentadiene were added to this solution. After 15 min, 39 g (0.34 moles) of 2,5-hexanedione were added dropwise, after which the cooling bath was removed and the reaction mixture was stirred for 2 h at room temperature. 200 ml of water and 200 ml of ether were then added. The ether layer was removed, washed with water and sodium chloride solution and then dried over Na$_2$SO$_4$. After removal of the solvent under vacuum and distillation at 65° C. and 0.1 mbar, compound 21 remained in the form of an orange-coloured oil (40 g; yield: 81%). $^1$H NMR (400 MHz, CDCl$_3$): δ=7.35–7.27 (m, 2H); 7.23 (d, J=7.6 Hz, 1H); 6.82 (m, 1H); 3.51 (s, 2H); 2.75 (s, 3H); 2.63 (s, 3H).

Example 20

Diisopropylphosphinotributylstannyl-4,7-dimethylindene, compound 22

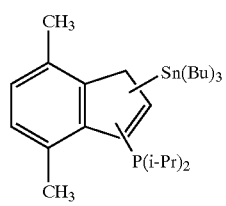

100 ml of ether were placed in a round-bottomed flask containing 5.0 g (0.035 moles) of 4,7-dimethylindene (compound 21); the solution was cooled to −20° C. 14 ml of a 2.5 molar solution of butyllithium in hexane (0.035 moles) were added over 5 min to form a yellow solution. After removal of the cooling bath, the solution was heated to room temperature and subsequently stirred for 1 h. After cooling of the reaction mixture to −20° C., 5.3 g (0.035 moles) of chlorodiisopropylphosphine were added over 5 min to form a precipitate. The cooling bath was then removed and the reaction mixture was stirred for 1 h at room temperature. After cooling to −20° C., 14.0 ml of a 2.5 molar solution of butyllithium in hexane (0.035 moles) were added dropwise. When the addition was complete, the cooling bath was removed and the solution was heated slowly to room temperature and stirred for 1.5 h. After cooling of the suspension to 0° C., 11.4 g of chlorotributyltin (0.035 moles) were added dropwise. The suspension formed was heated to room temperature and stirred for 1.5 h. The ether was removed under vacuum, the crude product was dissolved in hexane again, the solution was filtered and the filtrate was concentrated under vacuum to leave 16 g (yield: 83%) of compound 22 in the form of a heavy yellow oil. $^{31}$P NMR (161.9 MHz, CD$_2$Cl$_2$): δ=−9 ppm.

Example 21

Diisopropylphosphino-4,7-dimethylindenylzirconium trichloride, compound 23

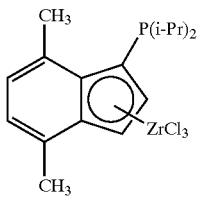

A solution of 16.0 g (0.029 moles) of compound 22 in $CH_2Cl_2$ (100 ml) was added over 10 min at −20° C. to a suspension of 6.4 g (0.029 moles) of 99.9% pure $ZrCl_4$ in 100 ml of $CH_2Cl_2$. When the addition was complete, the reaction mixture was heated slowly to room temperature over a period of two hours and then stirred at room temperature for a further 2 h. The solids were then filtered off and the solvent was removed under vacuum to leave the crude compound 23 in the form of an oil.

Example 22

Pyrrolyllithium, compound 24

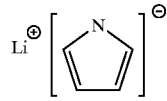

59 ml of a solution of butyllithium (2.5 molar in hexane, 0.148 moles) were added slowly at −20° C. to a solution of 9.9 g of pyrrole (0.148 moles) in 200 ml of hexane to form a white solid. The mixture was subsequently stirred for 2 hours at room temperature and the solid was isolated by filtration, washed with twice 20 ml of hexane and dried under vacuum. This procedure gave 6 g of compound 24 (56% of the theoretical yield). $^1H$ NMR (400 MHz, THF): δ=6.71 (s, 2H); 5.95 (s, 2H).

Example 23

1-Phenyl-2,3,4,5-tetramethylphosphole, compound 25

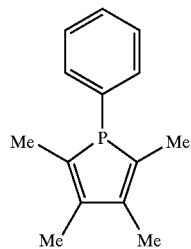

Following the instructions in Organometallics 7, (1988), 921, a solution of 11.7 g (0.216 moles) of 2-butyne in 150 ml of $CH_2Cl_2$ was added slowly to 15.3 g (0.115 moles) of $AlCl_3$ in $CH_2Cl_2$ (0° C.; 30 min). The mixture was subsequently stirred for 45 minutes at 0° C., the cooling bath was then removed and stirring was continued for a further one hour. The solution was then cooled to −50° C. and a solution of 21.4 g (0.12 moles) of phenyldichlorophosphine in $CH_2Cl_2$ was added over 20 minutes. The cooling bath was then removed and the dark red solution was subsequently stirred for one hour and then added at −30° C. to a solution of 27 g (0.13 moles) of tributylphosphine in 100 ml of $CH_2Cl_2$. The red colour disappeared immediately to leave a yellow solution. When the addition had ended, the solvent was removed under vacuum to leave a thick yellow oil. The oil was taken up with hexane and washed under an Ar atmosphere with saturated aqueous $NaHCO_3$ solution and $H_2O$. After drying over $MgSO_4$, the hexane was removed under vacuum to leave 18.2 g of compound 25 in the form of a clear oil (yield: 78%). $^1H$ NMR (400 MHz, $CDCl_3$): δ7.3 (m, 5H); 2.0 (m, 12H); $^{31}P$ NMR (161.9 MHz, $CDCl_3$): δ=16.8 ppm.

Example 24

Lithium 2,3,4,5-tetramethylphosphole, compound 26

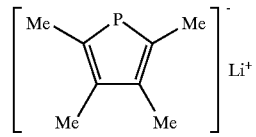

Following the instructions in Organometallics 7, (1988), 921, 0.52 g (0.074 moles) of lithium was added to a solution of 7 g (0.032 moles) of compound 33 in 150 ml of tetrahydrofuran (THF) and the mixture was stirred overnight. The resulting red solution was filtered through a frit to remove residual solids, and the filtrate was cooled to 0° C. A solution of 1.45 g (0.01 moles) of $AlCl_3$ in 20 ml of THF was then added dropwise and the solution was brought to room temperature. An aliquot was taken for analysis and the remaining solution was subsequently used directly. $^{31}P$ NMR (161.9 MHz, THF): δ=63.7 ppm.

Example 25

Tributylstannyldiethylphosphino-2-methylindene, compound 27

The procedure was analogous to Example 3 except that the 0.086 mole of indene was replaced with 0.086 mole of 2-methylindene.

Example 26

Diethylphosphino-2-methylindenezirconium trichloride, compound 28

The procedure was analogous to Example 4 except that $CH_2Cl_2$ was used in place of toluene as the solvent. The reaction temperature was 25° C. Purification was performed by Soxhlet extraction with $CH_2Cl_2$. Compound 28 was obtained in the form of an insoluble yellow solid in 78% of the theoretical yield.

Example 27

Catalyst Preparation

A red suspension of diphenylmethylphosphonium cyclopentadienide ($Ph_2MePcp$) in diethyl ether was reacted at -20° C. with an equimolar amount of butyllithium to give the ylide anion $Ph_2P(cp)(CH_2)^-Li^+$. A further equivalent of BuLi was added and the mixture was stirred for 1 hour at -20° C. and then for 1 hour at room temperature (RT). The yellow, slightly turbid solution was cooled to -20° C. again and 1 equivalent of $ZrCl_4$ as the THF complex was added carefully. After 2 hours, a dirty yellow solid had formed which, after isolation and drying under vacuum, was used for polymerization.

Example 28

Ethylene Polymerization 100 ml of dry, argon-saturated toluene were transferred to a 300 ml V4A steel autoclave which had been heated thoroughly under vacuum, a pressure of 5 bar of ethene was applied, the autoclave was heated to 90° C. and the catalyst (2.5 μmoles of the crude catalyst of Example 27 in 2.1 ml of toluene) was added with 2.5 mmol of methylaluminoxane (10% in toluene, preformed for 15 minutes at RT) by means of a pressure lock. After 1 hour, the polymerization was stopped with 5 ml of ethanol, the autoclave was depressurized, the contents of the autoclave were extracted by stirring for 1 hour in 500 ml of ethanol/concentrated hydrochloric acid (90/10) and the polymer was isolated by filtration, washed with ethanol until free of acid, and dried to constant weight at 90° C. in a vacuum drying cabinet.

Polymer yield: 1.9 g

Catalyst activity: 0.8 tonne of PE per mole of catalyst per hour

Intrinsic viscosity: 3.27 dl/g (orthodichlorobenzene, 140° C.)

DSC (2nd heating): $T_m=141°$ C., $\alpha H_m=189$ J/g

Example 29

Ethene/1-hexene copolymerization

The procedure was as in Example 28, 50 ml of toluene and 50 ml of 1-hexene being heated with a bath temperature of ca. 120° C. under 5 bar of ethene, 5 moles of the preformed catalyst of Example 28 being used and the internal pressure being adjusted to a constant value of 12.5 bar with ethene. The polymer yield after 1 hour was 5.3 g, corresponding to a catalyst activity of ca. 1 tonne of LLDPE per mole of catalyst per hour. The intrinsic viscosity, measured in ODCB at 140° C., was 0.71 dl/g. The DSC measurement in the 2nd heating gave $T_m=108°$ C. and $\Delta H_m=87$ J/g.

What is claimed is:

1. A π complex compound of transition metals of the formula

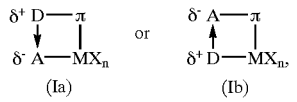

in which

π is a charged or electrically neutral π system which can be fused to one or two unsaturated or saturated five-membered or six-membered rings, and whose H atoms, in the fused or non-fused form, can be partially or completely replaced with identical or different radicals from the group consisting of unbranched or branched $C_1-C_{20}$-(cyclo)alkyl, $C_1-C_{20}$-halogeno(cyclo)alkyl, $C_2-C_{20}$-(cyclo)alkenyl, $C_1-C_{20}$-(cyclo)alkoxy, $C_7-C_{15}$-aralkyl and $C_6-C_{12}$-aryl, or replaced in one or two instances with D or A, D is a donor atom which, in the case of partial structure (Ia), is a substituent or part of the π system or is bonded to the π system via a spacer and, in the case of partial structure (Ib), is bonded to the transition metal, A is an acceptor atom which, in the case of partial structure (Ia), is bonded to the transition metal and, in the case of partial structure (Ib), is a substituent or part of the π system or is bonded to the π system via a spacer, the bonding of D or A to the transition metal taking place either directly or via a spacer, D and A being linked via a coordinate bond in such a way that the donor atom takes on a partial positive charge and the acceptor atom a partial negative charge, and it being possible for D and A in turn to carry substituents, M is a transition metal of subgroup III to VIII of the periodic table of the elements, including the lanthanides and actinides, X is one anion equivalent and n is the number zero, one, two, three or four, depending on the charges of M and π, D and A being specifically defined as follows:
  i) in formula (Ia):
    D is disubstituted N, P, As, Sb or Bi or monosubstituted O, S Se or Te, bonded to π via a spacer or directly, and
    A is B, Al, Ga or In, bonded to M via a spacer or directly; or
  ii) in formula (Ia), D and A together are one of the following groups bonded to π or M via a spacer or directly:

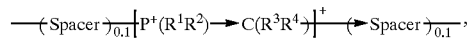
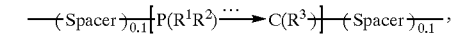
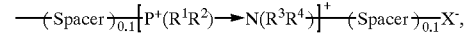
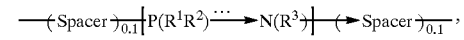

or

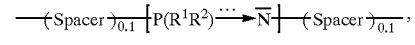

which represent phosphonium salts, phosphorus ylides, aminophosphonium salts and phosphinimines, or the corresponding ammonium salts and nitrogen ylides, arsonium salts and arsenic ylides, sulfonium salts and sulfur ylides, selenium salts and selenium ylides, the corresponding aminoarsonium salts and arsinimines, aminosulfonium salts and sulfimines, aminoselenium salts and selenimines,

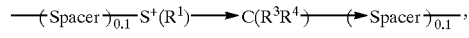
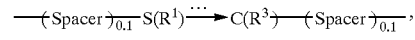
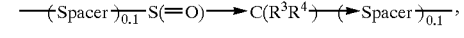
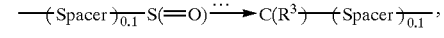

-continued

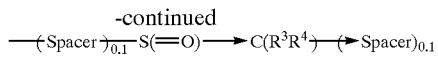

and the corresponding sulfimine structures; or
iii) in formula (Ib):
D is disubstituted N, P, As, Sb or Bi or monosubstituted O, S, Se or Te, bonded to M via a spacer or directly, and
A is disubstituted Al, Ga or In, bonded to π via a spacer or directly, or disubstituted B, bonded to π via a spacer,
$R^1$, $R^2$, $R^3$ or $R^4$ and the expression "substituted" independently of one another are $C_1$–$C_{20}$-(cyclo)alkyl, $C_1$–$C_{20}$-halogeno(cyclo)alkyl, $C_2$–$C_{20}$-(cyclo)alkenyl, $C_7$–$C_{15}$-aralkyl, $C_6$–$C_{12}$-aryl, $C_1$–$C_{20}$-(cyclo)alkoxy, $C_7$–$C_{15}$-aralkoxy, $C_6$–$C_{12}$-aryloxy, indenyl, halogen, 1-thienyl, disubstituted amino, trisubstituted silyl which can be bonded via —$CH_2$—, or phenylacetylenyl, and "Spacer" is a divalent silyl, germanyl, amino, phosphino, methylene, ethylene, propylene, disilylethylene or disiloxane group which can be monosubstituted to tetrasubstituted by $C_1$–$C_4$-alkyl, phenyl or $C_4$–$C_6$-cycloalkyl, and the element P, N, As, S or Se is bonded to π via the spacer or directly, a spacer being arranged between A and M in the case where D is part of the π system, and —$C(R^1)$= also occurring as a spacer in cases i) and ii).

2. A π complex compound according to claim 1, characterized in that the π system is a cyclopentadienyl skeleton from the group consisting of cyclopentadiene, substituted cyclopentadiene, indene, substituted indene, fluorene and substituted fluorene, in which 1 to 4 substituents from the group consisting of $C_1$–$C_{20}$-(cyclo)alkyl, $C_1$–$C_{20}$-(cyclo)alkoxy, halogen, $C_6$–$C_{12}$-aryl, D and A are present per cyclopentadiene ring or per fused benzene ring wherein fused aromatic rings may be partially or completely hydrogenated.

3. A π complex compound according to claim 1, wherein an element from the group consisting of N, P, As, O, S and Se is present as the donor atom D.

4. A π complex compound according to claim 1, wherein an element from the group consisting of B, Al, Ga and In is present as the acceptor atom A.

5. A π complex compound according to claim 1, wherein donor-acceptor bonds from the group consisting of N→B, N→Al, P→B, P→Al, O→B, O→Al, C=O→B and C=O→Al are present.

6. A π complex compound according to claim 1, wherein M is Sc, Y, La, Sm, Nd, Lu, Ti, Zr, Hf, Th, V, Nb, Ta or Cr.

7. A process for the homopolymerization or copolymerization of monomers from the group consisting of $C_2$–$C_{12}$-α-olefins, $C_4$–$C_{30}$-cycloolefins, $C_2$–$C_8$-alkynes, $C_4$–$C_8$-diolefins, $C_4$–$C_8$-vinyl esters and $C_8$–$C_{12}$-vinylaromatics, in the gas, solution, high-temperature solution, bulk, high-pressure or slurry phase, at −60° C. to +250° C. and 0.5 to 5000 bar, in the presence or absence of saturated or aromatic hydrocarbons or saturated or aromatic halogenohydrocarbons, and in the presence or absence of hydrogen wherein π complex compounds are used in an amount of $10^{-12}$ to $10^{-1}$ mole per mole of monomers, and it also being possible for the polymerization to be carried out in the presence of Lewis acids, Brönsted acids or Pearson acids or additionally in the presence of Lewis bases, wherein said π complex is of the formula

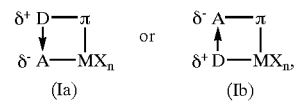

in which
π is a charged or electrically neutral π system which can be fused to one or two unsaturated or saturated five-membered or six-membered rings, and whose H atoms, in the fused or non-fused form, can be partially or completely replaced with identical or different radicals from the group consisting of unbranched or branched $C_1$–$C_{20}$-(cyclo)alkyl, $C_1$–$C_{20}$-halogeno(cyclo)alkyl, $C_2$–$C_{20}$-(cyclo)alkenyl, $C_1$–$C_{20}$-(cyclo)alkoxy, $C_7$–$C_{15}$-aralkyl and $C_6$–$C_{12}$-aryl, or replaced in one or two instances with D or A, D is a donor atom which, in the case of partial structure (Ia), is a substituent or part of the π system or is bonded to the π system via a spacer and, in the case of partial structure (Ib), is bonded to the transition metal, A is an acceptor atom which, in the case of partial structure (Ia), is bonded to the transition metal and, in the case of partial structure (Ib), is a substituent or part of the π system or is bonded to the π system via a spacer, the bonding of D or A to the transition metal taking place either directly or via a spacer, D and A being linked via a coordinate bond in such a way that the donor atom takes on a partial positive charge and the acceptor atom a partial negative charge, and it being possible for D and A in turn to carry substituents, M is a transition metal of subgroup III to VIII of the periodic table of the elements including the lanthanides and actinides, X is one anion equivalent and n is the number zero, one, two, three or four, depending on the charges of M and π, D and A being specifically defined as follows:
i) in formula (Ia):
D is disubstituted N, P, As, Sb or Bi or monosubstituted O, S Se or Te, bonded to π via a spacer or directly, and
A is B, Al, Ga or In, bonded to M via a spacer or directly; or
ii) in formula (Ia), D and A together are one of the following groups bonded to π or M via a spacer or directly:

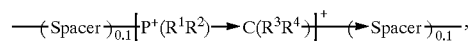

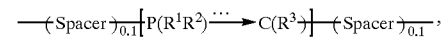

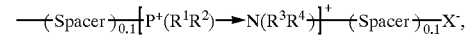

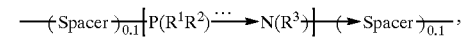

or

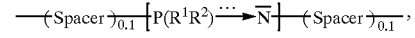

which represent phosphonium salts, phosphorus ylides, aminophosphonium salts and phosphinimines,
or the corresponding ammonium salts and nitrogen ylides, arsonium salts and arsenic ylides, sulfonium salts and sulfur ylides, selenium salts and selenium ylides, the corresponding aminoarsonium salts and arsinimines, aminosulfonium salts and sulfimines, aminoselenium salts and selenimines,

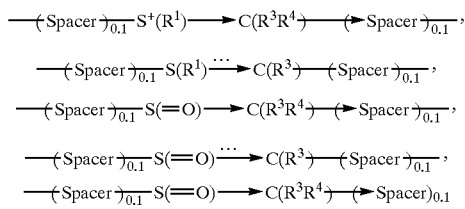

and the corresponding sulfimine structures; or iii) in formula (Ib):
D is disubstituted N, P, As, Sb or Bi or monosubstituted O, S, Se or Te, bonded to M via a spacer or directly, and A is disubstituted Al, Ga or In, bonded to π via a spacer or directly, or disubstituted B, bonded to π via a spacer, $R^1$, $R^2$, $R^3$ or $R^4$ and the expression "substituted" independently of one another are $C_1$–$C_{20}$-(cyclo)alkyl, $C_1$–$C_{20}$-halogeno(cyclo)alkyl, $C_2$–$C_{20}$-(cyclo)alkenyl, $C_7$–$C_{15}$-aralkyl, $C_6$–$C_{12}$-aryl, $C_1$–$C_{20}$-(cyclo)alkoxy, $C_7$–$C_{15}$-aralkoxy, $C_6$–$C_{12}$-aryloxy, indenyl, halogen, 1-thienyl, disubstituted amino, trisubstituted silyl which can be bonded via —$CH_2$—, or phenylacetylenyl, and "Spacer" is a divalent silyl, germanyl, amino, phosphino, methylene, ethylene, propylene, disilylethylene or disiloxane group which can be monosubstituted to tetrasubstituted by $C_1$–$C_4$-alkyl, phenyl or $C_4$–$C_6$-cycloalkyl, and the element P, N, As, S or Se is bonded to π via the spacer or directly, a spacer being arranged between A and M in the case where D is part of the π system, and —$C(R^1)$= also occurring as a spacer in cases i) and ii).

8. A process according to claim 7, wherein the π complex compound is used together with an aluminoxane, alane or alanate, a borane or borate and optionally other cocatalysts and/or metal alkyls as the catalyst system.

9. A process according to claim 7, the π complex compound is of the formulae

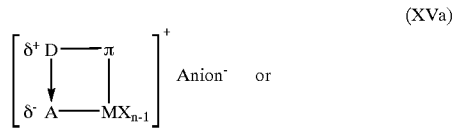

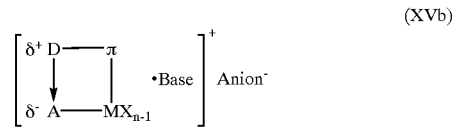

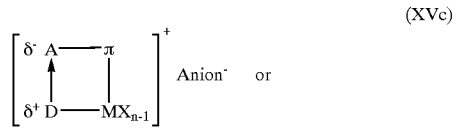

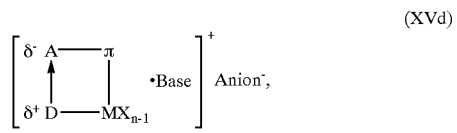

in which
anion represents the entire bulky, poorly coordinating anion and
base represents a Lewis base, are used.

10. A process according to claim 7 for the preparation of HDPE, LLDPE with butylene, hexene or octene as comonomer, and terpolymers.

* * * * *